United States Patent
Tsuyuki

(10) Patent No.: US 10,893,793 B2
(45) Date of Patent: Jan. 19, 2021

(54) OBJECTIVE OPTICAL SYSTEM AND ENDOSCOPE DEVICE INCLUDING THE SAME

(71) Applicant: OLYMPUS CORPORATION, Hachioji (JP)

(72) Inventor: Hiroshi Tsuyuki, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 99 days.

(21) Appl. No.: 16/185,064

(22) Filed: Nov. 9, 2018

(65) Prior Publication Data
US 2019/0076001 A1 Mar. 14, 2019

Related U.S. Application Data

(63) Continuation of application No. PCT/JP2017/015575, filed on Apr. 18, 2017.

(30) Foreign Application Priority Data

May 27, 2016 (JP) ................................ 2016-106314

(51) Int. Cl.
*A61B 1/00* (2006.01)
*A61B 1/05* (2006.01)
(Continued)

(52) U.S. Cl.
CPC ........ *A61B 1/00096* (2013.01); *A61B 1/0005* (2013.01); *A61B 1/00009* (2013.01);
(Continued)

(58) Field of Classification Search
CPC .... G02B 27/14; G02B 27/144; G02B 27/283; G02B 27/145; G02B 27/0172;
(Continued)

(56) References Cited

U.S. PATENT DOCUMENTS 6,985,170 B1 1/2006 Tsuyuki
8,994,802 B2 3/2015 Suga et al.
(Continued)

FOREIGN PATENT DOCUMENTS

CN 103957770 A 7/2014
JP 2000137172 A 5/2000
(Continued)

OTHER PUBLICATIONS

International Search Report (ISR) dated Jul. 18, 2017 issued in International Application No. PCT/JP2017/015575.
(Continued)

*Primary Examiner* — William R Alexander
*Assistant Examiner* — Sharrief I Broome
(74) *Attorney, Agent, or Firm* — Holtz, Holtz & Volek PC

(57) ABSTRACT

An objective optical system includes a lens group and an optical path splitting element. The optical path splitting element is disposed on an optical path of the lens group, the optical path splitting element includes an optical path splitting surface configured to form a first optical path and a second optical path, an optical path length in the first optical path is different from an optical path length in the second optical path, a sum total of the number of transmissions of light and the number of reflections of light in the second optical path is larger than a sum total of the number of transmissions of light and the number of reflections of light in the first optical path, and an optical surface satisfying following conditional expression (1) is disposed on the first optical path, $$0.8 \leq MR650/MR550 \leq 0.9 \quad (1).$$

14 Claims, 13 Drawing Sheets

(51) Int. Cl.
*G02B 23/24* (2006.01)
*A61B 1/04* (2006.01)
*A61B 1/06* (2006.01)
*G02B 27/12* (2006.01)
*G02B 23/26* (2006.01)

(52) U.S. Cl.
CPC .......... *A61B 1/00188* (2013.01); *A61B 1/042* (2013.01); *A61B 1/051* (2013.01); *A61B 1/0669* (2013.01); *G02B 23/243* (2013.01); *G02B 27/126* (2013.01); *G02B 23/2469* (2013.01); *G02B 23/26* (2013.01)

(58) Field of Classification Search
CPC .............. G02B 27/142; G02B 27/1066; G02B 27/1006; G02B 27/141; G02B 27/0101; G02B 27/10; G02B 27/126; G02B 2027/0125; G02B 2027/0174; G02B 26/0833; G02B 27/0081; G02B 27/108; G02B 27/1086; G02B 27/123; G02B 5/30; H01S 3/0057; H01S 5/4012; H01S 5/405; H01S 3/005; H01S 3/09408; H01S 3/1618; H01S 5/005; H01S 5/4062; H01S 5/4087; H01S 2301/03; H01S 3/00; H01S 3/0014; H01S 3/0071; H01S 3/0092; H01S 3/067; H01S 3/06708; H01S 3/06712; H01S 3/06733; H01S 3/0675; H01S 3/06791
See application file for complete search history.

(56) References Cited

U.S. PATENT DOCUMENTS

| | | | |
|---|---|---|---|
| 2015/0098132 A1* | 4/2015 | Nagaishi | G02B 30/00 |
| | | | 359/629 |
| 2015/0335232 A1* | 11/2015 | Ito | G02B 23/26 |
| | | | 362/13 |
| 2017/0042414 A1* | 2/2017 | Ito | A61B 1/063 |
| 2017/0187943 A1* | 6/2017 | Tsuyuki | A61B 1/00188 |
| 2017/0231502 A1* | 8/2017 | Nagaoka | G02B 23/2484 |
| | | | 600/476 |

FOREIGN PATENT DOCUMENTS

| | | |
|---|---|---|
| JP | 2014103597 A | 6/2014 |
| WO | 2013190785 A1 | 12/2013 |

OTHER PUBLICATIONS

Written Opinion dated Jul. 18, 2017 issued in International Application No. PCT/JP2017/015575.

International Preliminary Report on Patentability (IPRP) (and English language translation thereof) and Written Opinion dated Nov. 27, 2018 issued in counterpart International Application No. PCT/JP2017/015575.

Chinese Office Action (and English language translation thereof) dated May 20, 2020 issued in counterpart Chinese Application No. 201780028158.1.

* cited by examiner

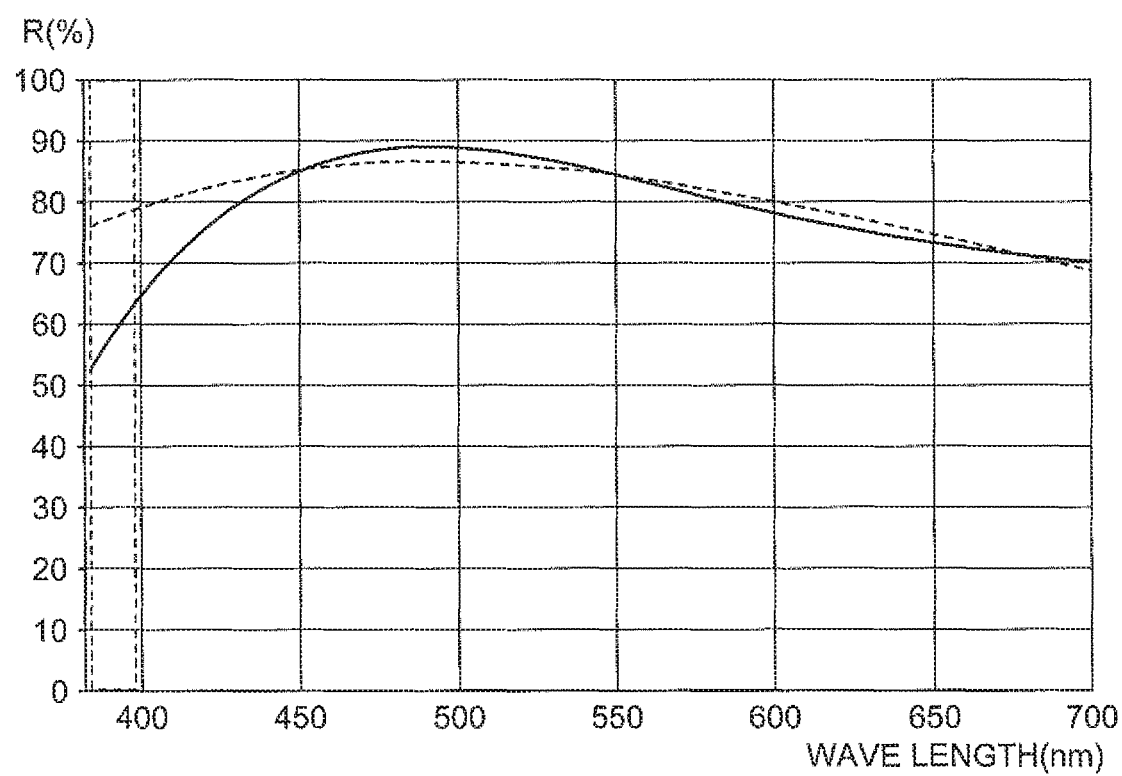

BEFORE CORRECTION

AFTER CORRECTION

OBJECTIVE OPTICAL SYSTEM AND ENDOSCOPE DEVICE INCLUDING THE SAME

CROSS-REFERENCE TO RELATED APPLICATION

The present application is a continuation application of PCT/JP2017/015575 filed on Apr. 18, 2017 which is based upon and claims the benefit of priority from Japanese Patent Application No. 2016-106314 filed on May 27, 2016; the entire contents of which are incorporated herein by reference.

BACKGROUND OF THE INVENTION

Field of the Invention

The present invention relates to an objective optical system and an endoscope device including the same.

Description of the Related Art

An optical system forming two optical images from an objective optical system is disclosed in Japanese Unexamined Patent Application Publication No. 2014-103597. In the optical system, a splitting element is disposed on an image side of the objective optical system. The light beam emitted from the objective optical system is made incident on the splitting element. In the splitting element, the light beam made incident on the splitting element is divided into a reflection light beam and a transmitted light beam by a first surface.

The transmitted light beam transmitted through the first surface is reflected by a second surface located on an optical path. Thereafter, an optical image is formed by the transmitted light beam.

The reflection light beam reflected by the first surface is reflected by a mirror disposed on an optical path. By this reflection, the reflection light beam is reflected toward the first surface. The reflection light beam is transmitted through the first surface. Thereafter, an optical image is formed by the reflection light beam.

The traveling direction of the reflection light beam after transmission of the first surface is equal to the traveling direction of the transmitted light beam after reflection with the second surface. Accordingly the optical image formed by the reflection light beam and the optical image formed by the transmitted light beam are formed in the same direction.

In the optical system disclosed in Japanese Unexamined Patent Application Publication No. 2014-103597, two optical paths are formed by the splitting element. The first optical path is an optical path from the first surface to the optical image of the transmitted light beam. The second optical path is an optical path from the first surface to the optical image of the reflection light beam. The optical path length in the first optical path is equal to the optical path length in the second optical path. Accordingly, two optical images in focus are formed in different positions on a same plane.

In imaging of the optical image, imaging is performed through a color filter. The color filter is formed of a plurality of filter elements. The filter elements are divided into, for example, three groups. The first group is formed of filter elements transmitting red light, the second group is formed of filter elements transmitting green light, and the third group is formed of filter elements transmitting blue light.

In Japanese Unexamined Patent Application Publication No. 2014-103597, the color filter used for imaging is different between imaging of one optical image and imaging of the other optical image. In this manner, two images having different colors are acquired. Moreover, by composing the two images, the color reproducibility of the image is improved.

It is also possible to make the optical path length in the first optical path slightly different from the optical path length in the second optical path. In this case, two optical images in focus are formed in front of and behind the same plane. The shift quantities of the optical images from the same plane are slight. For this reason, on the same plane, two optical images in focus only in parts of the region are formed.

The two optical images have different in-focus regions. The two optical images are imaged, and thereby two images are acquired. Thereafter, only the in-focus regions are extracted from the two imaged images, and the extracted regions are composed. In this manner, it is possible to acquire an image with a large depth of field.

SUMMARY OF THE INVENTION

An objective optical system according to at least some embodiments of the present invention comprises:
a lens group configured to form an image of an object; and
an optical path splitting element disposed on an image side of the lens group, wherein
the optical path splitting element is disposed on an optical path of the lens group,
the optical path splitting element includes an optical path splitting surface configured to form a first optical path and a second optical path,
the first optical path is formed on a line extended from the optical path of the lens group,
the second optical path is formed to cross the first optical path,
an optical path length in the first optical path is different from an optical path length in the second optical path,
a sum total of a number of transmissions of light and a number of reflections of light in the second optical path is larger than a sum total of a number of transmissions of light and a number of reflections of light in the first optical path, and
an optical surface satisfying following conditional expression (1) is disposed on the first optical path, $$0.8 \leq MR650/MR550 \leq 0.9 \tag{1}$$

where,
MR550 is reflectivity at a wavelength of 550 nm, and
MR650 is reflectivity at a wavelength of 650 nm.

An endoscope device according to the present invention comprises:
the objective optical system;
an image pickup element; and
an image processing device.

BRIEF DESCRIPTION OF THE DRAWINGS

FIG. 5 is a diagram illustrating spectral characteristics of an optical surface;

DETAILED DESCRIPTION OF THE INVENTION

The following is an explanation of an objective optical system according to the present embodiment and an endoscope device according to the present embodiment, with respect to the reason why such configuration is adopted and the function thereof, with reference to the drawings. The present invention is not limited with the objective optical system according to the following embodiment or the endoscope device according to the present embodiment.

An objective optical system according to the present embodiment includes a lens group configured to form an image of an object, and an optical path splitting element disposed on an image side of the lens group, wherein the optical path splitting element is disposed on an optical path of the lens group, the optical path splitting element includes an optical path splitting surface configured to form a first optical path and a second optical path, the first optical path is formed on a line extended from the optical path of the lens group, the second optical path is formed to cross the first optical path, an optical path length in the first optical path is different from an optical path length in the second optical path, a sum total of a number of transmissions of light and a number of reflections of light in the second optical path is larger than a sum total of a number of transmissions of light and a number of reflections of light in the first optical path, and an optical surface satisfying following conditional expression (1) is disposed on the first optical path, $$0.8 \leq MR650/MR550 \leq 0.9 \quad (1)$$

where,

MR550 is reflectivity at a wavelength of 550 nm, and
MR650 is reflectivity at a wavelength of 650 nm.

Figure 1:
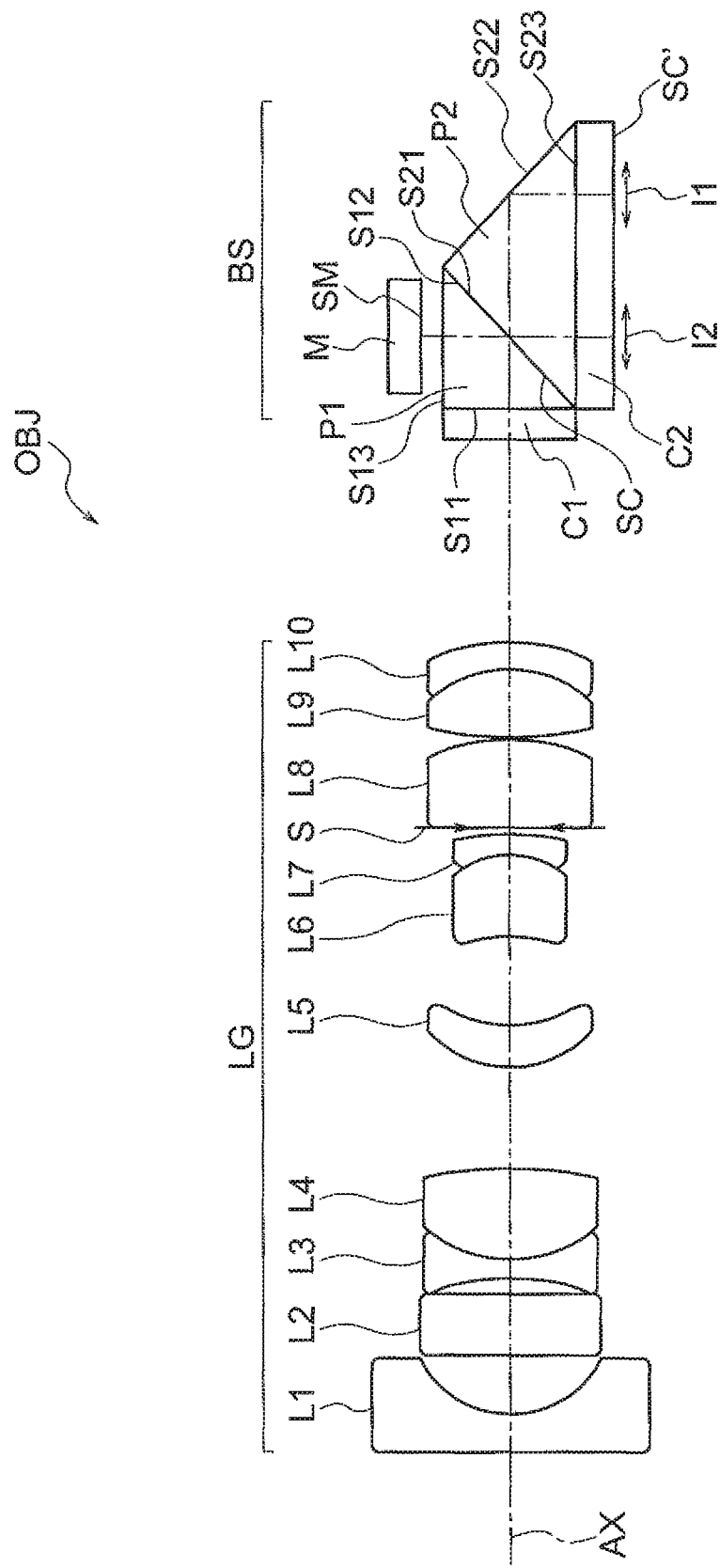
FIG. 1 is a diagram illustrating a configuration of an objective optical system according to the present embodiment.

FIG. 1 illustrates a configuration of the objective optical system according to the present embodiment. An objective optical system OBJ includes a lens group LG and an optical path splitting unit BS. The lens group LG includes a plurality of lenses L1 to L10 and an aperture stop S. An optical image of an object is formed by the lens group LG.

The optical path splitting unit BS is disposed on an image side of the lens group LG. The optical path splitting unit BS includes a cover glass C1, a prism P1, a prism P2, a mirror M, and a cover glass C2. Each of the prism P1 and the prism P2 is a triangular prism. The optical path splitting element is formed of the prism P1 and the prism P2.

The cover glass C1 is cemented to an optical surface S11 of the prism P1. The prism P1 is cemented to the prism P2.

A cemented surface SC is formed of an optical surface S12 of the prism P1 and an optical surface S21 of the prism P2.

The mirror M is disposed such that an optical surface SM is opposed to an optical surface S13 of the prism P1. The cover glass C2 is cemented to an optical surface S23 of the prism P2.

The optical path splitting unit BS is disposed on an optical path of the lens group LG. Light (hereinafter referred to as "imaging light") emitted from the lens group LG is made incident on the optical path splitting unit BS. The imaging light is transmitted through the cover glass C1 and made incident on the optical surface S11. Because the optical surface S11 is a transmission surface, the imaging light is transmitted through the optical surface S11.

Thereafter, the imaging light is made incident on the cemented surface SC. The cemented surface SC is disposed such that a normal line of the surface has an angle of 45° with respect to an optical axis AX. The imaging light made incident on the cemented surface SC is divided into light (hereinafter referred to as "imaging light 1") transmitted through the cemented surface SC and light (hereinafter referred to as "imaging light 2") reflected with the cemented surface SC.

The imaging light 1 and the imaging light 2 travel in mutually different directions. When an optical path in which the imaging light 1 travels is referred to as a first optical path and an optical path in which the imaging light 2 travels is referred to as a second optical path, the first optical path and the second optical path are formed with the cemented surface SC. As just described, the cemented surface SC serves as an optical path splitting surface.

The first optical path is formed on a line extended from the optical path of the lens group LG. The second optical path is formed to cross the first optical path. In FIG. 1, the second optical path is orthogonal to the first optical path.

The sum total (hereinafter referred to as "first sum total") of the number of transmissions of light and the number of reflections of light in the first optical path is different from the sum total (hereinafter referred to as "second sum total") of the number of transmissions of light and the number of reflections of light in the second optical path.

The cemented surface SC, an optical surface S22, the optical surface S23, and an optical surface SC' are located on the first optical path.

The imaging light 1 transmitted through the cemented surface SC is made incident on the optical surface S22. The optical surface S22 is a reflection surface. The imaging light 1 is reflected by the optical surface S22, and made incident on the optical surface S23. The optical surface S23 is a transmission surface. The imaging light 1 is transmitted through the optical surface S23, and made incident on the cover glass C2. The imaging light 1 reaches the optical surface Sc'. The optical surface SC' is a transmission surface. An optical image I1 is formed in the vicinity of the optical surface Sc'.

In the first optical path, reflection of light occurs in the optical surface S22, and transmission of light occurs in the cemented surface SC, the optical surface S23, and the optical surface SC'. Accordingly, the first sum total is four.

The cemented surface SC, the optical surface S13, the optical surface SM, the optical surface S23, and the optical surface SC' are located on the second optical path.

The imaging light 2 reflected with the cemented surface SC is made incident on the optical surface S13. The optical surface S13 is a transmission surface. The imaging light 2 is transmitted through the optical surface S13, and made incident on the optical surface SM of the mirror M. The optical surface SM is a reflection surface. The imaging light 2 is reflected by the optical surface SM, and made incident on the optical surface S13.

The imaging light 2 is transmitted through the optical surface S13, and made incident on the cemented surface SC. In the cemented surface SC, the imaging light 2 is divided into light transmitted through the cemented surface SC and light reflected by the cemented surface SC.

The imaging light 2 transmitted through the cemented surface SC is made incident on the optical surface S23. The imaging light 2 is transmitted through the optical surface S23, and made incident on the cover glass C2. The imaging light 2 reaches the optical surface SC'. An optical image I2 is formed in the vicinity of the optical surface SC'.

In the second optical path, reflection occurs in the cemented surface SC and the optical surface SM, and transmission occurs in the optical surface S13, the cemented surface SC, the optical surface S23, and the optical surface SC'. Because transmission occurs twice in the optical surface S13, the second sum total is seven.

As just described, in the objective optical system according to the present embodiment, the second sum total is larger than the first sum total.

In endoscopes, observation of the inside of the body is performed. The subject in the body looks reddish in many cases. Moreover, an image pickup element is used for imaging of the subject. The sensitivity of an image pickup element increases as the wavelength increases. For this reason, the sensitivity for red light is higher than sensitivity for blue light and green light.

A spectral characteristic is a characteristic in which transmissivity or reflectivity in an optical surface is indicated as the function of a wavelength. A first spectral characteristic is a spectral characteristic determined on all the optical surfaces located on the first optical path. A second spectral characteristic is a spectral characteristic determined on all the optical surfaces located on the second optical path.

In the second spectral characteristic, when the transmissivity and/or the reflectivity is low in a long wavelength region, the transmissivity and/or the reflectivity in the long wavelength region is lower in the second spectral characteristic than in the first spectral characteristic. In this case, when the second sum total is larger than the first sum total, decrease in transmissivity and/or decrease in reflectivity in the long wavelength region is remarkable in the second spectral characteristic.

For this reason, in the objective optical system according to the present embodiment, the optical surface satisfying the conditional expression (1) described above is located on the first optical path.

Figure 2A:
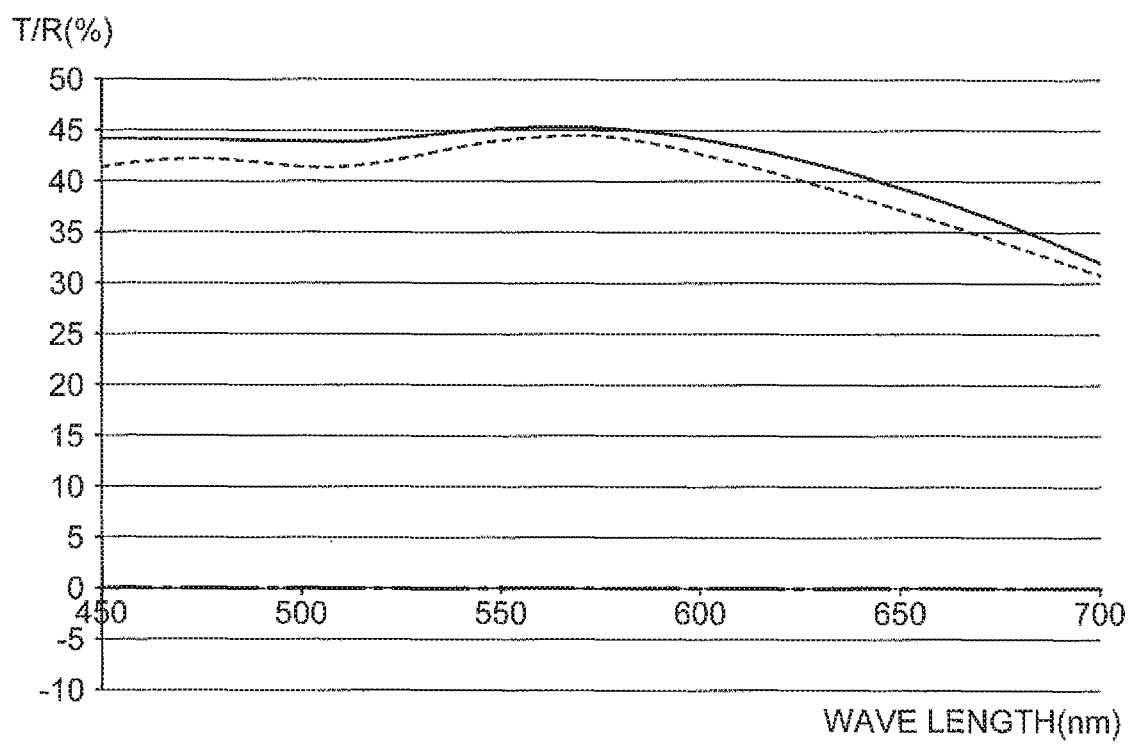
FIG. 2A and FIG. 2B are diagrams illustrating spectral characteristics.
Figure 2B:
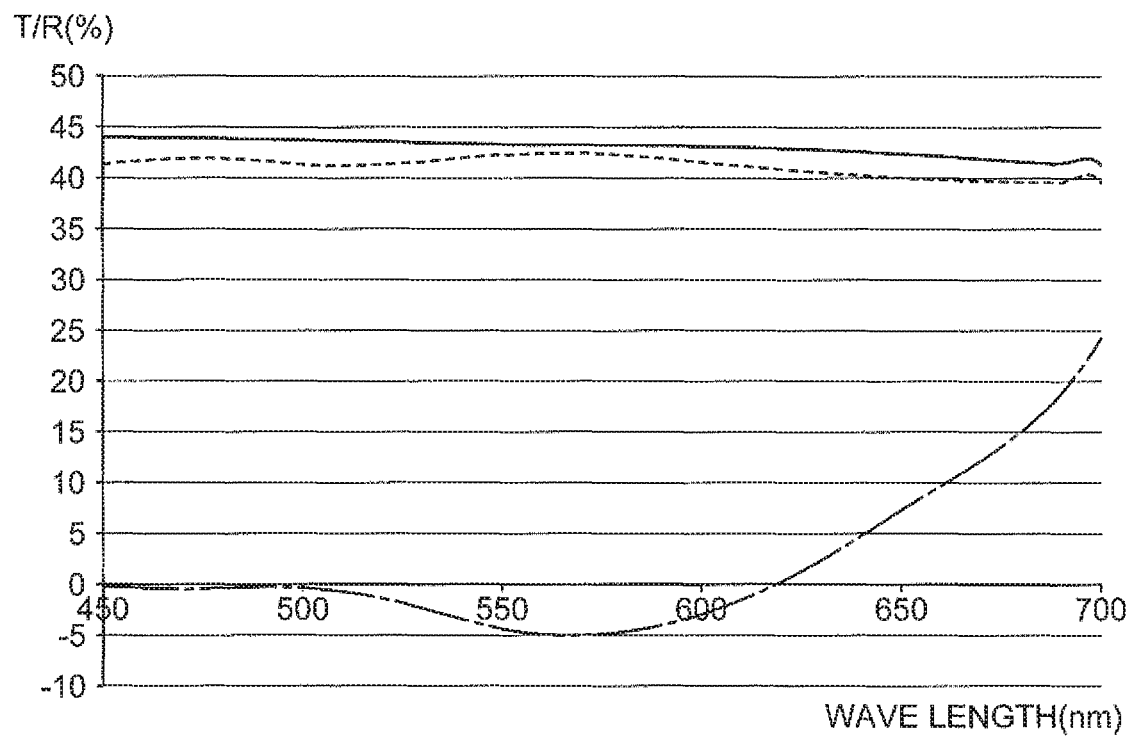

FIG. 2A and FIG. 2B are diagrams illustrating spectral characteristics. FIG. 2A illustrates a case where an optical surface satisfying the conditional expression (1) is disposed on the first optical path, and FIG. 2B illustrates a case where an optical surface that fails to satisfy the conditional expression (1) is disposed on the first optical path.

In FIG. 2A, a solid line indicates the spectral characteristic (reflectivity) of the optical surface satisfying the conditional expression (1), a broken line indicates the first spectral characteristic (transmissivity), and an alternate long and short dash line indicates a difference between the first spectral characteristic and the second spectral characteristic.

In the optical surface satisfying the conditional expression (1), the reflectivity gradually decreases from 600 nm to 700 nm, as illustrated in FIG. 2A. With this change, also in the first spectral characteristic, the transmissivity gradually decreases from 600 nm to 700 nm.

As described above, decrease in transmissivity and/or decrease in reflectivity in the long wavelength region is remarkable in the second spectral characteristic. Accordingly, although it is not illustrated in FIG. 2A, the transmissivity gradually decreases from 600 nm to 700 nm also in the second spectral characteristic.

In FIG. 2A, the decrease of the transmissivity in the first spectral characteristic is substantially equal to the decrease of the transmissivity in the second spectral characteristic at each of the wavelengths. For this reason, the difference between the first spectral characteristic and the second spectral characteristic is substantially zero in the range from 450 nm to 700 nm (in FIG. 2A, the difference substantially overlaps the horizontal axis indicating zero).

By contrast, in the optical surface that fails to satisfy the conditional expression (1), the reflectivity is substantially fixed from 450 nm to 700 nm, as illustrated in FIG. 2B. With this condition, also in the first spectral characteristic, the transmissivity is substantially fixed from 450 nm to 700 nm.

In this case, the transmissivity from 600 nm to 700 nm is larger in the first spectral characteristic than that in the second spectral characteristic. For this reason, the difference between the first spectral characteristic and the second spectral characteristic gradually increases on the side of the wavelength longer than 620 nm, and exceeds 20% at 700 nm.

As just described, by locating the optical surface satisfying the conditional expression (1) on the first optical path, it is possible to set the first spectral characteristic to be substantially equal to the second spectral characteristic. As a result, it is possible to form a plurality of optical images having a small difference in brightness and/or a small difference in tone.

Figure 3:
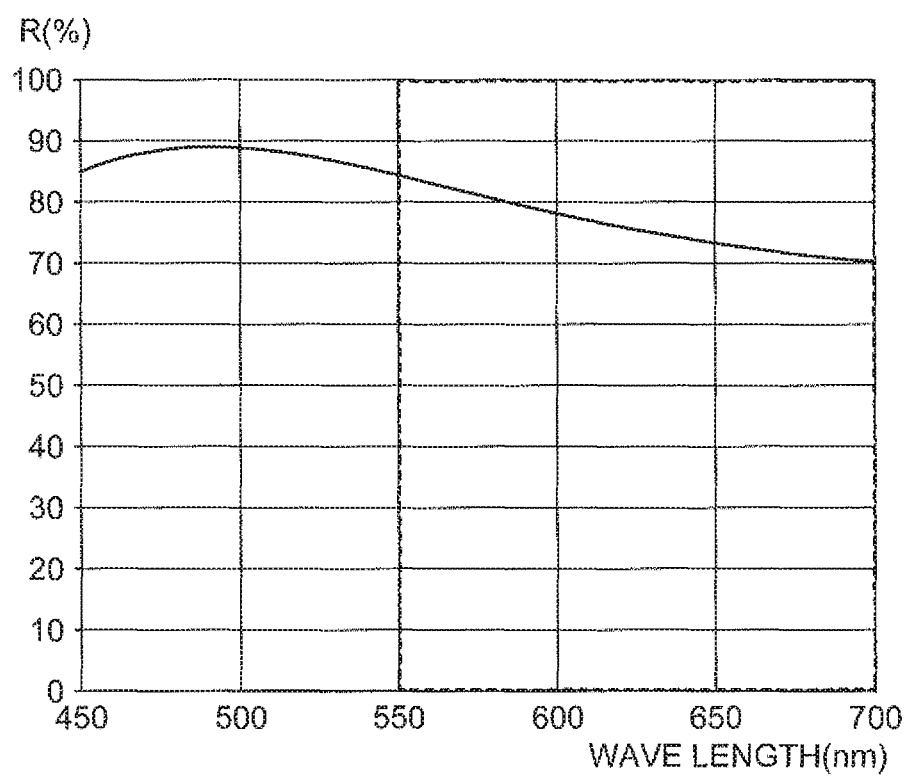
FIG. 3 is a diagram illustrating spectral characteristics of an optical surface.

In the objective optical system OBJ illustrated in FIG. 1, the optical surface S22 serves as an optical surface satisfying the conditional expression (1). FIG. 3 illustrates the spectral characteristics in the optical surface S22. As illustrated in FIG. 3, in the optical surface S22, the reflectivity gradually decreases in a range enclosed with broken lines, that is, from 550 nm to 700 nm.

In the spectral characteristics illustrated in FIG. 3, "MR650/MR550=0.87" is satisfied. As just described, by forming the optical surface S22 as the optical surface satisfying the conditional expression (1), it is possible to set the brightness and/or the tone to be substantially equal between the optical image I1 and the optical image I2.

As described above, in the method of acquiring an image with a large depth of field, only in-focus regions are extracted from a plurality of images, and composition of the extracted regions is performed. In the objective optical system according to the present embodiment, it is possible to reduce the difference in brightness and the difference in tone in a plurality of optical images. Accordingly, it is possible to reduce the unevenness in brightness and the difference in tone in the composite image.

Moreover, when the optical path length in the first optical path is set equal to the optical path length in the second optical path, two optical images in focus are formed in different positions in the same plane. As described above, in the method for improving the color reproducibility of the image, image composition using a plurality of images is performed. In the objective optical system according to the present embodiment, it is possible to reduce the difference in brightness and the difference in tone in a plurality of optical images. Accordingly, it is possible to further improve the color reproducibility of the composite image.

The cover glass C1 and the cover glass C2 are not always necessary. Moreover, by forming the optical surface S13 as a reflection surface, it is possible to reflect the imaging light 2. Accordingly, the mirror M is not always necessary.

In the objective optical system according to the present embodiment, it is preferable that the optical surface satisfying the following conditional expression (2) be positioned on the first optical path:

$$0.75 \leq MRB \leq 0.80 \quad (2)$$

where,

MRB is reflectivity at a wavelength of 390 nm.

One of the observation methods with an endoscope is a method of performing observation using light of a narrow wavelength region (hereinafter referred to as "narrow-band observation"). In narrow-band observation, for example, light of a wavelength band from 400 nm to 430 nm is used.

In the second spectral characteristic, when the transmissivity and/or the reflectivity are low in the short wavelength region, the transmissivity and/or the reflectivity in the short wavelength region are lower in the second spectral characteristic than in the first spectral characteristic. In this case, when the second sum total is larger than the first sum total, decrease in transmissivity and/or decrease in reflectivity in the short wavelength region is remarkable in the second spectral characteristic.

In the objective optical system according to the present embodiment, the optical surface satisfying the conditional expression (2) described above is located on the first optical path.

Figure 4A:
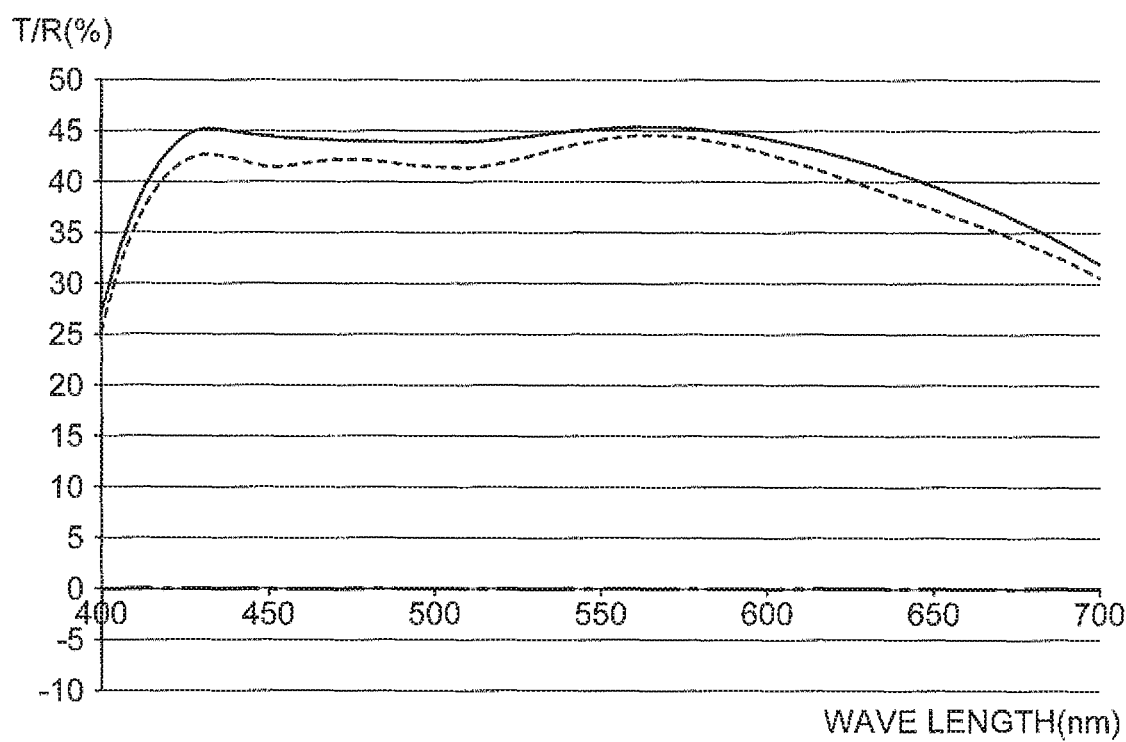
FIG. 4A and FIG. 4B are diagrams illustrating spectral characteristics.
Figure 4B:
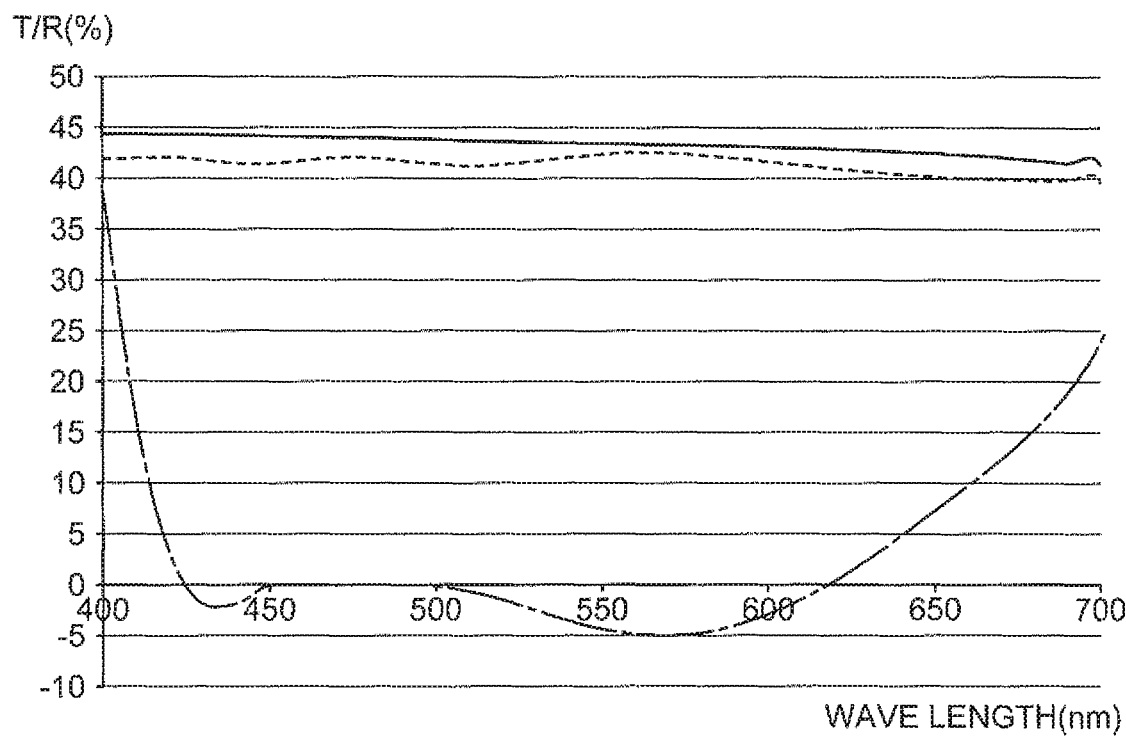

FIG. 4A and FIG. 4B are diagrams illustrating spectral characteristics. FIG. 4A illustrates a case where an optical surface satisfying the conditional expression (2) is disposed on the first optical path, and FIG. 4B illustrates a case where an optical surface that fails to satisfy the conditional expression (2) is disposed on the first optical path.

In FIG. 4A, a solid line indicates a spectral characteristic (reflectivity) of the optical surface satisfying the conditional expression (2), a broken line indicates the first spectral characteristic (transmissivity), and an alternate long and short dash line indicates a difference between the first spectral characteristic and the second spectral characteristic.

In the optical surface satisfying the conditional expression (2), the reflectivity gradually decreases from 430 nm to 400 nm, as illustrated in FIG. 4A. With this change, also in the first spectral characteristic, the transmissivity gradually decreases from 430 nm to 400 nm.

As described above, decrease in transmissivity and/or decrease in reflectivity in the short wavelength region is remarkable in the second spectral characteristic. Accordingly, although it is not illustrated in FIG. 4A, the transmissivity gradually decreases from 430 nm to 400 nm also in the second spectral characteristic.

In FIG. 4A, the decrease of the transmissivity in the first spectral characteristic is substantially equal to the decrease of the transmissivity in the second spectral characteristic at each of the wavelengths. For this reason, the difference between the first spectral characteristic and the second spectral characteristic is substantially zero in the range from 430 nm to 400 nm (in FIG. 4A, the difference substantially overlaps the horizontal axis indicating zero).

By contrast, in the optical surface that fails to satisfy the conditional expression (2), the reflectivity is substantially fixed from 400 nm to 700 nm, as illustrated in FIG. 4B. With this condition, also in the first spectral characteristic, the transmissivity is substantially fixed from 400 nm to 700 nm.

In this case, the transmissivity from 430 nm to 400 nm is larger in the first spectral characteristic than that in the second spectral characteristic. For this reason, the difference between the first spectral characteristic and the second spectral characteristic gradually increases on the side of the wavelength shorter than 430 nm, and reaches 40% at 400 nm.

As just described, by locating the optical surface satisfying the conditional expression (2) on the first optical path, it is possible to set the first spectral characteristic to be substantially equal to the second spectral characteristic. As a result, it is possible to form a plurality of optical images having a small difference in brightness and/or a small difference in tone also in narrow-band observation.

In the objective optical system according to the present embodiment, it is preferable that the optical surface satisfying the conditional expression (1) and the optical surface satisfying the conditional expression (2) be the same optical surface.

By providing one optical surface with two spectral characteristics, it is possible to miniaturize the optical path splitting element. Moreover, it is possible to shorten the manufacturing process.

In the objective optical system OBJ illustrated in FIG. 1, the optical surface S22 serves as the optical surface satisfying the conditional expression (2). As described above, it is possible to form the optical surface S22 as the optical surface satisfying the conditional expression (1). As just described, it is possible to form the optical surface S22 as the optical surface satisfying the conditional expression (1) and the conditional expression (2).

FIG. 5 illustrates spectral characteristics in the optical surface S22. A solid line indicates a case where the optical surface S22 satisfies the conditional expression (1) but fails to satisfy the conditional expression (2), and a broken line illustrates a case where the optical surface S22 satisfies the conditional expression (1) and the conditional expression (2).

For example, it is assumed that observation of an optical image formed with light of a wavelength band from 450 nm to 700 nm is performed in ordinary observation, and observation of an optical image formed with light of a wavelength band from 400 nm to 430 nm is performed in narrow-band observation.

When the optical surface S22 has the spectral characteristic indicated with the solid line, in the optical surface S22, the reflectivity gradually decreases from 550 nm to 700 nm. Accordingly, in ordinary observation, it is possible to form a plurality of optical images having a small difference in brightness and a small difference in tone. In the spectral characteristic indicated with the solid line, "MR650/MR550=0.87" is satisfied.

By contrast, the reflectivity gradually decreases in a range enclosed with broken lines, that is, from 430 nm to 400 nm, but the reflectivity is smaller than 75%. Accordingly, in narrow-band observation, it is difficult to form a plurality of optical images having a small difference in brightness and a small difference in tone.

By contrast, when the optical surface S22 has the spectral characteristic indicated with the broken line, in the optical surface S22, the reflectivity gradually decreases from 550 nm to 700 nm. In the spectral characteristic indicated with the broken line, "MR650/MR550=0.88" is satisfied. Accordingly, in ordinary observation, it is possible to form a plurality of optical images having a small difference in brightness and a small difference in tone.

Moreover, the reflectivity gradually decreases from 430 nm to 400 nm, and the reflectivity is equal to or larger than 75%. In the spectral characteristic indicated with the broken line, "MRB=0.78" is satisfied. Accordingly, also in narrow-band observation, it is possible to form a plurality of optical images having a small difference in brightness and a small difference in tone.

In the objective optical system according to the present embodiment, it is preferable that the following conditional expression (3) be satisfied:

$$-0.15 \leq (B-A)/B \leq 0.15 \quad (3)$$

where,

B is transmissivity in a predetermined wavelength range of the first optical path, A is transmissivity in a predetermined wavelength range of the second optical path, and the predetermined wavelength range is a range from a wavelength of 400 nm to a wavelength of 700 nm.

By satisfying the conditional expression (3), it is possible to form a plurality of optical images having a small difference in brightness and a small difference in tone in both ordinary observation and narrow-band observation.

It is preferable that the following conditional expression (3') be satisfied instead of the conditional expression (3).

$$-0.10 \leq (B-A)/B \leq 0.10 \quad (3')$$

It is preferable that the following conditional expression (3") be satisfied instead of the conditional expression (3).

$$-0.05 \leq (B-A)/B \leq 0.05 \quad (3'')$$

In the objective optical system according to the present embodiment, it is preferable that a reflection surface and a ¼ wavelength plate be positioned on the second optical path, the ¼ wavelength plate be disposed between the optical path splitting surface and the reflection surface, and the optical surface have a characteristic of transmitting P-polarized light and reflecting S-polarized light.

Figure 6:
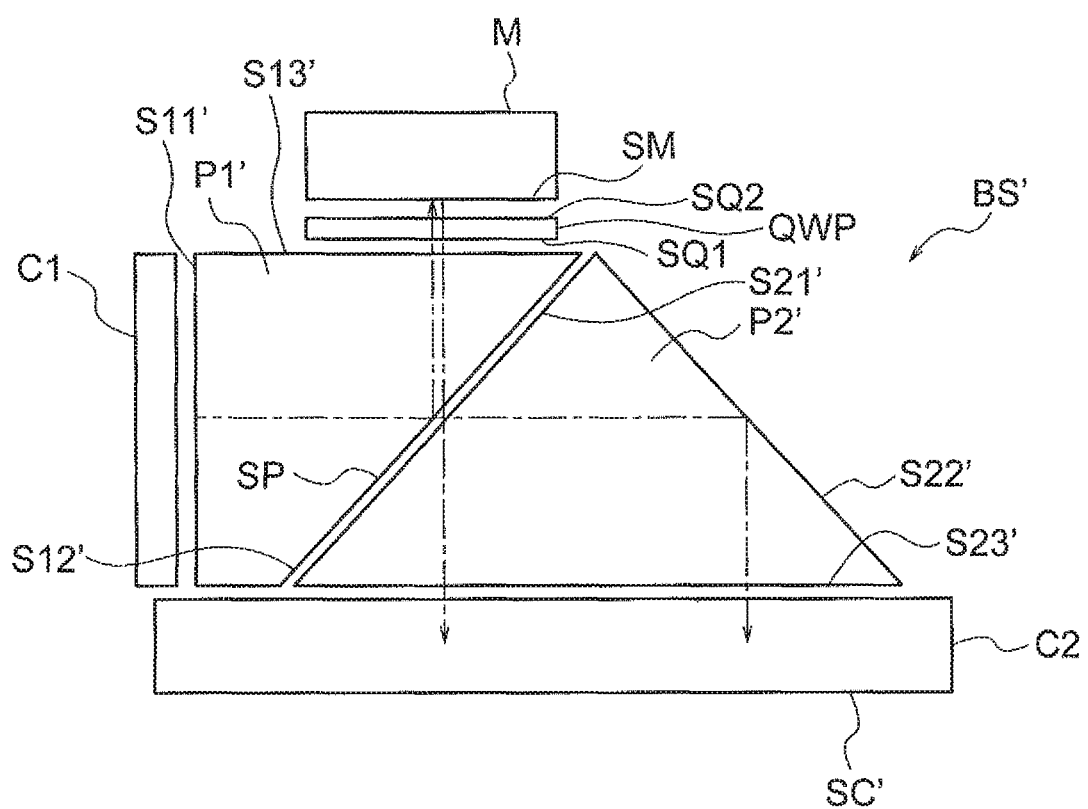
FIG. 6 is a diagram illustrating an optical path splitting unit.

FIG. 6 is a diagram illustrating an optical path splitting unit. An optical path splitting unit BS' is disposed on the image side of the lens group. The optical path splitting unit BS' includes the cover glass C1, a prism P1', a prism P2', a ¼ wavelength plate QWP, the mirror M, and the cover glass C2. The optical splitting element is formed of the prism P1' and the prism P2'.

FIG. 6 illustrates that the cover glass C1 and the prism P1' are spatially apart from each other. However, actually, the cover glass C1 and the prism. P1' are cemented as explained below. The same is applicable to the prism P2', the ¼ wavelength plate QWP, and the cover glass C2.

The cover glass C1 is cemented to an optical surface S11' of the prism P1'. The prism P1' is cemented to the prism P2'. An optical surface SP is formed of an optical surface S12' of the prism P1' and an optical surface S21' of the prism P2'.

The mirror M is disposed such that an optical surface SM is opposed to an optical surface S13' of the prism P1'. The ¼ wavelength plate QWP is disposed between the mirror M and the prism P1'. The cover glass C2 is cemented to an optical surface S23' of the prism P2'.

The imaging light is made incident on the optical path splitting unit BS'. The imaging light is transmitted through the cover glass C1, and made incident on the optical surface S11'. Because the optical surface S11' is a transmission surface, the imaging light is transmitted through the optical surface S11'.

Thereafter, the imaging light is made incident on the optical surface SP. The optical surface SP is disposed such that a normal line of the surface has an angle of 45° with respect to the optical axis. The optical path splitting unit BS' is a polarization beam splitter. Therefore, in the optical surface SP, P-polarized light is transmitted, and S-polarized light is reflected.

Suppose that P-polarized light is imaging light 1, and S-polarized light is imaging light 2. The imaging light 1 and the imaging light 2 travel in mutually different directions. When the optical path in which the imaging light 1 travels is referred to as the first optical path and the optical path in which the imaging light 2 travels is referred to as the second optical path, the first optical path and the second optical path are formed with the optical surface SP. As just described, the optical surface SP serves as an optical path splitting surface.

The optical surface SP, the optical surface S22', the optical surface S23', and the optical surface SC' are located on the first optical path. In the first optical path, reflection of light occurs in the optical surface S22', and transmission of light occurs in the optical surface SP, the optical surface S23', and the optical surface SC'. Accordingly, the first sum total is four.

The ¼ wavelength plate QWP is located on the second optical path. The imaging light 2 reflected with the optical surface SP is linearly-polarized light. The imaging light 2 is transmitted through the ¼ wavelength plate QWP and converted into circularly-polarized light. The imaging light 2 is reflected by the optical surface SM of the mirror M, and transmitted through the ¼ wavelength plate QWP again.

The imaging light 2 is transmitted through the ¼ wavelength plate QWP and converted into linearly-polarized light. The imaging light 2 emitted from the ¼ wavelength plate QWP has a polarization direction orthogonal to the S direction. Specifically, the imaging light 2 is P-polarized light. Accordingly, the imaging light 2 is transmitted through the optical surface SP.

As just described, in the optical path splitting unit BS', most of the S-polarized imaging light 2 reflected with the optical surface SP is changed to the P-polarized imaging light 2, and transmitted through the optical surface SP. Accordingly, in the second optical path, it is possible to form an optical image with a small loss of light quantity.

The optical surface SP, the optical surface S13', an optical surface SQ1, an optical surface SQ2, the optical surface SM, the optical surface S23', and the optical surface SC' are located on the second optical path. In the second optical path, reflection of light occurs in the optical surface SP and the optical surface SM, and transmission of light occurs in the optical surface SP, the optical surface S13', the optical surface SQ1, the optical surface SQ2, the optical surface S23', and the optical surface SC'. Light is transmitted twice in each of the optical surface S13', the optical surface SQ1, and the optical surface SQ2. Accordingly, the second sum total is 11.

As just described, in the objective optical system according to the present embodiment, the second sum total is larger than the first sum total.

However, in the objective optical system according to the present embodiment, the optical surface satisfying the conditional expression (1) is located on the first optical path. Accordingly, it is possible to set the first spectral characteristic and the second spectral characteristic substantially equal to each other. As a result, it is possible to form a plurality of optical images with a small difference in brightness and a small difference in tone.

To set the first spectral characteristic and the second spectral characteristic substantially equal to each other, it suffices to provide the optical surface located on the first optical path with a specific spectral characteristic, or provide the optical surface located on the second optical path with a specific spectral characteristic.

However, when the polarization beam splitter is used as the optical path splitting element and the ¼ wavelength plate QWP is disposed on the second optical path, it is more preferable to dispose the optical surface satisfying the conditional expression (1) on the first optical path. In this manner, it is easily accomplished to set the transmissivity from 600 nm to 700 nm substantially equal between the first spectral characteristic and the second spectral characteristic.

In the ¼ wavelength plate QWP, conversion from linearly-polarized light into circularly-polarized light or conversion from circularly-polarized light into linearly-polarized light is performed. However, the conversion is not accurately performed at wavelengths other than the specific wavelength. Specifically, at wavelengths other than the specific wavelength, linearly-polarized light and/or circularly-polarized light is converted into elliptically-polarized light. The elliptic degree differs according to the wavelength. As just described, the ¼ wavelength plate QWP has a wavelength dispersion characteristic.

In the optical path splitting unit BS, it is preferable that the imaging light 2 traveling from the ¼ wavelength plate QWP toward the optical surface SP be converted into linearly-polarized light. However, because the ¼ wavelength plate QWP has a wavelength dispersion characteristic, in some wavelengths, the imaging light 2 traveling from the ¼ wavelength plate QWP toward the optical surface SP is not linearly-polarized light. For this reason, a loss of light quantity occurs when the imaging light 2 is transmitted through the optical surface SP. Moreover, the magnitude of the loss of light quantity differs according to the wavelength.

As a method for equalizing the magnitude of the loss of light quantity in the ¼ wavelength plate at each of the wavelengths, there is a method of using a plurality of wavelength plates in combination. However, even this method has a limit in performance. Moreover, the size of the objective optical system increases by using a plurality of wavelength plates.

As just described, when the ¼ wavelength plate QWP is disposed on the second optical path, it is difficult to set the first spectral characteristic and the second spectral characteristic substantially equal to each other, by providing the ¼ wavelength plate QWP with a specific spectral characteristic. Accordingly, it is preferable to provide the optical surface located on the first optical path with a specific spectral characteristic.

Figure 7:
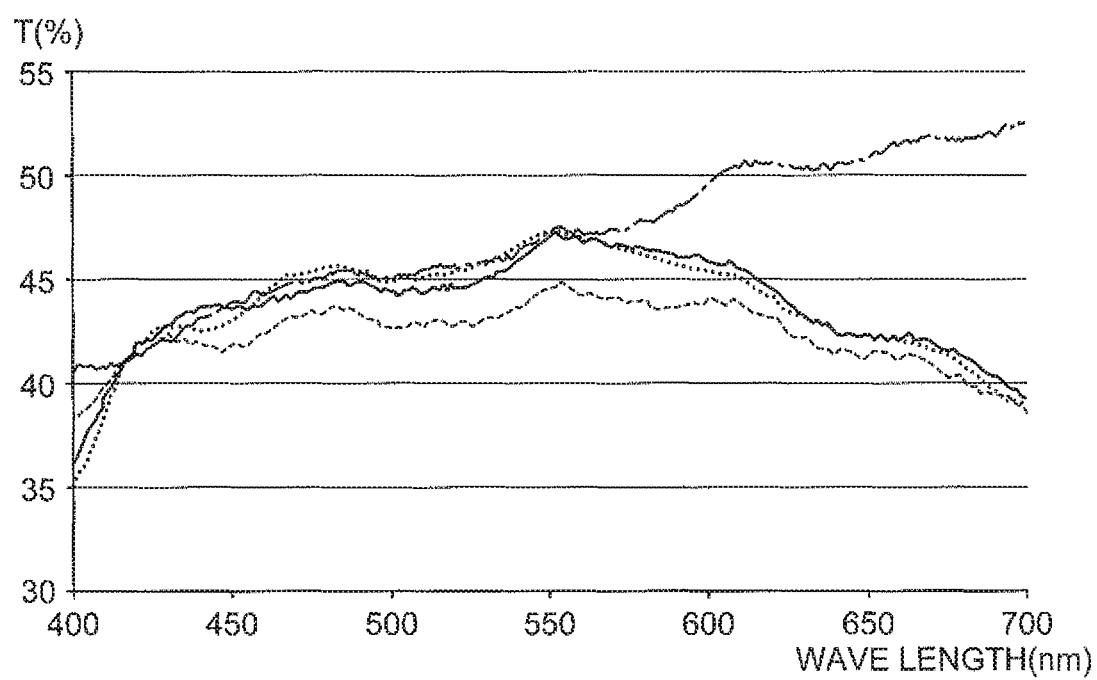
FIG. 7 is a diagram illustrating spectral characteristics of a first example.

An example of spectral characteristics in the objective optical system according to the present embodiment is shown. FIG. 7 illustrates spectral characteristics in a first example. In the first example, a polarization beam splitter is used as the optical path splitting element. Moreover, the value of the transmissivity at each of wavelengths is the value in a case where the incident light quantity on the polarization beam splitter is set to 100%.

In FIG. 7, a solid line and a dotted line indicate spectral characteristics in the first example, and an alternate long and short dash line and a broken line indicate spectral characteristics in a conventional example. The solid line indicates a spectral characteristic in the first optical path, and the dotted line indicates a spectral characteristic in the second optical path. The alternate long and short dash line indicates a spectral characteristic in the first optical path, and the broken line indicates a spectral characteristic in the second optical path.

As illustrated in FIG. 7, in the conventional example, the transmissivity in the first optical path and the transmissivity in the second optical path are markedly different from each other on the long-wavelength side, and also different on the short-wavelength side. Accordingly, a difference in brightness and/or a difference in tone occurs on the long-wavelength side in ordinary observation, and a difference in brightness and/or a difference in tone occurs on the short-wavelength side in narrow-band observation.

By contrast, in the first example, the spectral characteristic of the first optical path and the spectral characteristic of the second optical path are substantially the same. Accordingly, according to the first example, it is possible to form a plurality of optical images with a small difference in brightness and a small difference in tone in both ordinary observation and narrow-band observation.

Figure 8:
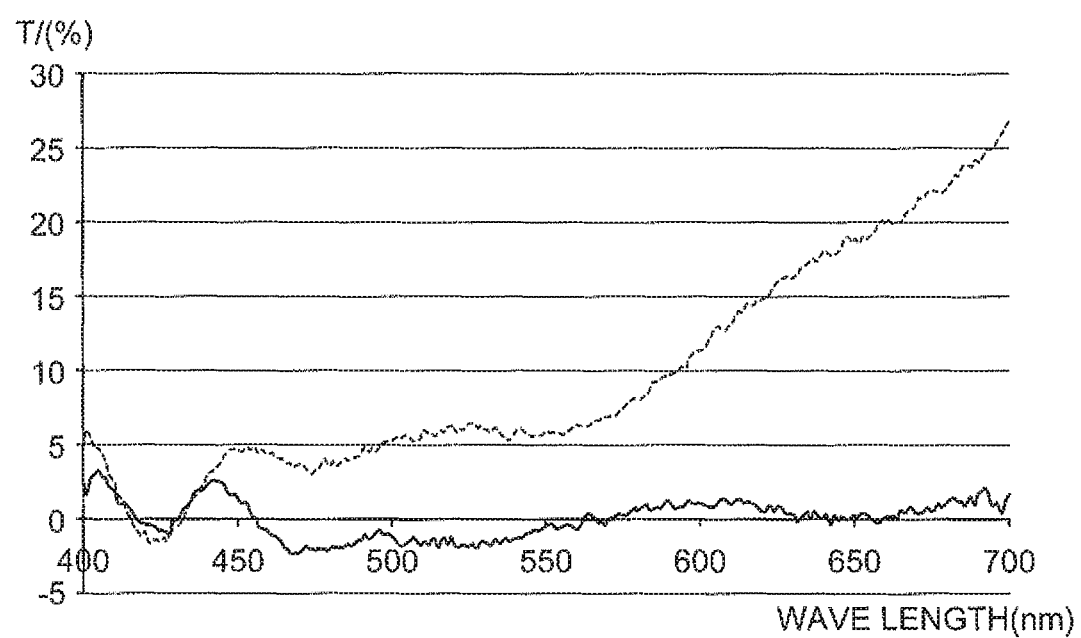
FIG. 8 is a diagram illustrating spectral characteristics of a second example.

FIG. 8 illustrates spectral characteristics in a second example. In the second example, a polarization beam splitter is used as the optical path splitting element. Moreover, the value of the transmissivity at each of wavelengths is the value in the case where the incident light quantity on the polarization beam splitter is set to 100%.

In FIG. 8, a solid line indicates a spectral characteristic in the second example, and a broken line indicates a spectral characteristic in the conventional example. In FIG. 8, a difference between the first spectral characteristic and the second spectral characteristic is illustrated.

The difference between the first spectral characteristic and the second spectral characteristic is acquired from "(B−A)/B". As illustrated in FIG. 8, in the conventional example, the value of (B−A)/B exceeds 25% at most. Accordingly, in ordinary observation, a difference in brightness and a difference in tone occurs on the long-wavelength side.

By contrast, in the second example, the value of (B−A)/B falls within a range of ±5%. Specifically, the conditional expression (3) is satisfied. Therefore, according to the second example, it is possible to form a plurality of optical images having a small difference in brightness and a small difference intone in both ordinary observation and narrow-band observation.

Figure 9:
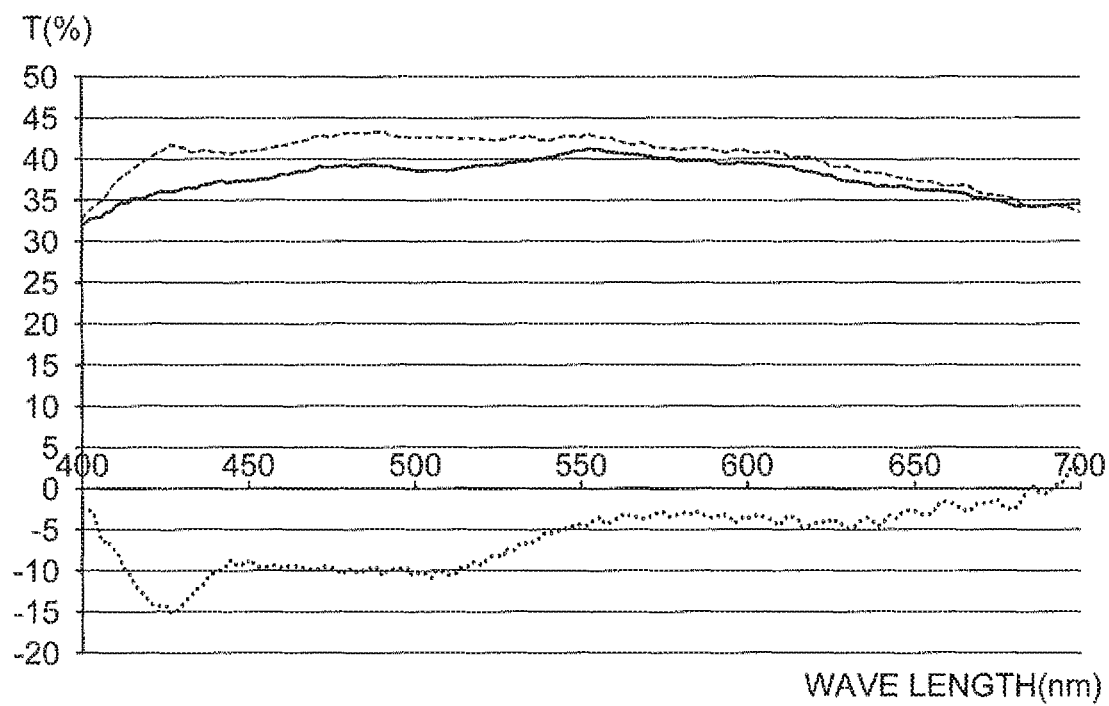
FIG. 9 is a diagram illustrating spectral characteristics of a third example.
Figure 10:
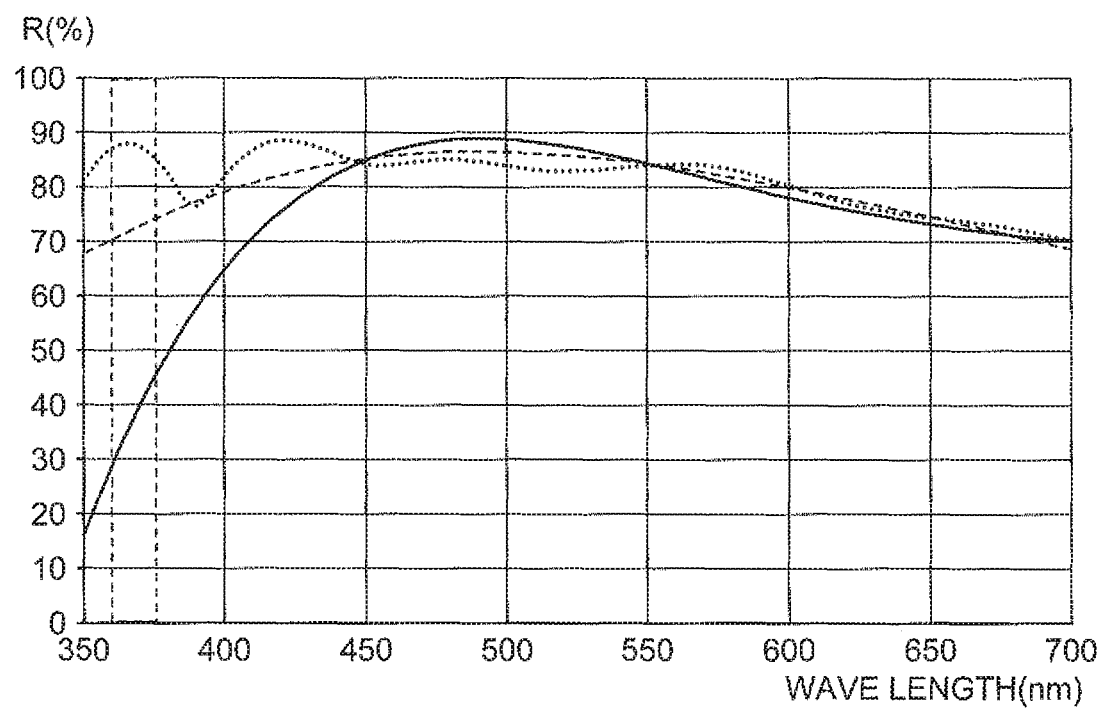
FIG. 10 is a diagram illustrating spectral characteristics.

FIG. 9 illustrates spectral characteristics in a third example. In the third example, a polarization beam splitter is used as the optical path splitting element. Moreover, the value of the transmissivity at each of wavelengths is the value in the case where the incident light quantity on the polarization beam splitter is set to 100%.

In FIG. 9, a solid line, a broken line, and a dotted line indicate spectral characteristics in the third example. The solid line indicates a spectral characteristic in the first optical path, the broken line indicates a spectral characteristic in the second optical path. The dotted line indicates a difference between the first spectral characteristic and the second spectral characteristic. The difference between the first spectral characteristic and the second spectral characteristic is acquired from "(B−A)/B".

In the third example, the spectral characteristic of the first optical path and the spectral characteristic of the second optical path are substantially equal to each other. Moreover, in the third example, the value of "(B−A)/B" falls within a range of −15% or less. Specifically, the conditional expression (3) is satisfied. For this reason, according to the third example, it is possible to form a plurality of optical images having a small difference in brightness and a small difference in tone in both ordinary observation and narrow-band observation.

In the objective optical system according to the present embodiment, it is preferable that a depolarization element be disposed between the lens group and the optical path splitting element.

When the optical path splitting element is a polarization beam splitter, the light quantity of the imaging light 1 and the light quantity of the imaging light 2 depend on the polarization state of the imaging light made incident on the optical surface SP. For example, when the imaging light is P-polarized light, the whole imaging light is transmitted through the optical surface SP. Therefore, although the imaging light 1 occurs, no imaging light 2 occurs. As a result, the optical image I1 is formed, but no optical image I2 is formed.

For this reason, a depolarization element is disposed between the lens group and the optical path splitting element. In this manner, it is possible to set the imaging light made incident on the optical surface SP to light to generate the imaging light 1 and the imaging light 2.

It is preferable that the depolarization element generate light having random polarization directions. The depolarization element is, for example, a ¼ wavelength plate.

In the objective optical system according to the present embodiment, it is preferable that a dielectric multilayer film be formed on the optical surface satisfying the conditional expression (1).

Examples of a reflection coating include a coating with a metal film, such as an aluminum coating and a silver coating. In the aluminum coating and the silver coating, the reflectivity at each of the wavelengths is substantially the same. In the aluminum coating and the silver coating, it is difficult to reduce the reflectivity in a specific wavelength region.

For this reason, it is preferable that a dielectric multilayer film be formed on the optical surface satisfying the conditional expression (1).

In a dielectric multilayer film, it is possible to reduce the reflectivity in a specific wavelength region. Accordingly, it is possible to easily achieve the optical surface satisfying the conditional expression (1). It is desirable that the number of layers of the dielectric film be 10 or less, from the viewpoint of prevention of contamination and the viewpoint of stability of the spectral characteristic.

In the objective optical system according to the present embodiment, it is preferable that the optical surface satisfying the conditional expression (1) include a metal reflective film, and the dielectric multilayer film be formed on the metal reflective film.

With this structure, it is possible to reduce the reflectivity in the specific wavelength region even when the number of layers in the dielectric film is reduced.

It is preferable that the objective optical system according to the present embodiment include an optical surface which satisfy the following conditional expression (4):

$$0.85 \leq MRUV \leq 0.9 \tag{4}$$

where,

MRUV is reflectivity at a wavelength of 365 nm of the first optical path.

As illustrated in FIG. 1, the optical image I1 and the optical image I2 are formed in the vicinity of the optical surface SC'. For this reason, by positioning the image pickup surface of the image pickup element here, it is possible to image the optical image I1 and the optical image I2. Because the image pickup surface of the image pickup element is provided with a cover glass, the cover glass C2 serves as the cover glass of the image pickup element.

The cover glass C2 is cemented to the prism P1 such that stable imaging is performed. In the cementing, a thermosetting adhesive and/or an ultraviolet-curing adhesive is used. In the case of using a thermosetting adhesive, heat is transmitted to the prism P1, the prism P2, and the image pickup element.

In the optical path splitting unit BS illustrated in FIG. 1, the cover glass C1 is cemented to the prism P1. The cover glass C1 has relatively high resistance to heat. Accordingly, even when a thermosetting adhesive is used for bonding of the cover glass C2 to the prism P1, influence of heat on the cover glass C1 is not large.

In the optical path splitting unit BS illustrated in FIG. 9, the ¼ wavelength plate QWP is positioned on the second optical path. Although the ¼ wavelength plate QWP is apart from the prism P2 in FIG. 9, actually the ¼ wavelength plate QWP is cemented to the prism P2.

Examples of the ¼ wavelength plate includes a crystalline-type ¼ wavelength plate and a polymer film-type ¼ wavelength plate. A polymer film ¼ wavelength plate is used in many cases. However, a polymer film is highly affected by heat. For this reason, the polymer film-type ¼ wavelength plate is easily affected by heat. The polymer film-type ¼ wavelength plate may be deformed or incur change in polarization characteristic due to heat, for example.

In a thermosetting adhesive, generally, the temperature in curing is 80° C. to 140° C., and the time for curing is 30 to 60 minutes. For this reason, when the polymer film-type ¼ wavelength plate is cemented to the prism P1 in advance, it is difficult to use a thermosetting adhesive for cementing the cover glass C2 to the prism P1.

For this reason, when the polymer film-type ¼ wavelength plate is cemented to the prism P1 in advance, it is preferable that an ultraviolet-curing adhesive be used for cementing the cover glass C2 to the prism P1. In this manner, even when the ¼ wavelength plate is of a polymer film type, no fear of deformation and/or change in polarization characteristic occurs.

Moreover, it is preferable that an ultraviolet-curing adhesive with a curing wavelength of 365 nm be used as the ultraviolet-curing adhesive. In this case, it is preferable that the optical surface satisfying the conditional expression (4) be included.

In a case of falling below a lower limit value of the conditional expression (4), when ultraviolet rays are applied to the adhesive through the optical surface, no ultraviolet rays having sufficient brightness are applied to the adhesive. As a result, adhesion failure may occur.

In a case of exceeding an upper limit value of the conditional expression (4), the energy generated with the ultraviolet rays becomes too large. When the image pickup element includes a color filter, the color filter may be damaged.

In the objective optical system according to the present embodiment, it is preferable that the optical surface satisfying the conditional expression (1) and the optical surface satisfying the conditional expression (4) be the same optical surface.

By providing one optical surface with two spectral characteristics, it is possible to miniaturize the optical path splitting element. Moreover, it is possible to shorten the manufacturing process.

In the objective optical system according to the present embodiment, it is preferable that the optical surface satisfying the conditional expression (2) and the optical surface satisfying the conditional expression (4) be the same optical surface.

By providing one optical surface with two spectral characteristics, it is possible to miniaturize the optical path splitting element. Moreover, it is possible to shorten the manufacturing process.

The endoscope device according to the present embodiment includes the objective optical system as described above, an image pickup element, and an image processing device.

According to the endoscope device of the present embodiment, it is possible to acquire an image with a small difference in brightness and a small difference in tone in at least one of ordinary observation and narrow-band observation.

In the explanation described above, when the second sum total is larger than the first sum total, decrease in transmissivity and/or decrease in reflectivity is more remarkable in the second spectral characteristic than in the first spectral characteristic. However, the same phenomenon may occur also in a case where the number of reflections in the first sum total is different from the number of reflections in the second sum total, even when the second sum total is equal to the first sum total.

Moreover, the same phenomenon may occur also in a case where the second sum total is equal to the first sum total and the number of reflections in the first sum total is equal to the number of reflections in the second sum total. For example, it is assumed that a mirror and a parallel plate are disposed on the first optical path, and a mirror and a ¼ wavelength plate are disposed on the second optical path.

In this case, both the number of reflections in the first optical path and the number of reflections in the second optical path are 1. Moreover, both the number of transmissions in the first optical path and the number of transmissions in the second optical path are 2. Accordingly, both the first sum total and the second sum total are 3. As a result, in this example, the second sum total is equal to the first sum total, and the number of reflections in the first sum total is equal to the number of reflections in the second sum total.

In this example, when the spectral characteristic of the mirror disposed on the first optical path is different from the spectral characteristic of the mirror disposed on the second optical path, the first spectral characteristic is different from the second spectral characteristic. Moreover, even when the spectral characteristics of the two mirrors are the same, when the spectral characteristic of the parallel plate disposed on the first optical path is different from the spectral characteristic of the ¼ wavelength plate disposed on the second optical path, the first spectral characteristic is different from the second spectral characteristic.

As just described, the difference between the first spectral characteristic and the second spectral characteristic is not caused by only the difference in number of reflections or number of transmissions, but affected by the spectral characteristic of the mirror surface disposed on the optical path and/or the spectral characteristic of the transmission element.

Moreover, the optical surface largely decreasing the transmissivity and/or reflectivity may be disposed on the first optical path. In such a case, decrease in transmissivity and/or decrease in reflectivity is remarkable more in the first spectral characteristic than in the second spectral characteristic.

In view of the above, it suffices to dispose an optical surface satisfying the conditional expression (1) and/or an optical surface satisfying the conditional expression (2) in the optical path in which decrease in transmissivity and/or decrease in reflectivity appears less remarkably.

An endoscope device according to the present embodiment comprises: an objective optical system; an image pickup element; and an image processing device, wherein the objective optical system includes: a lens group configured to form an image of an object; and an optical path splitting element disposed on an image side of the lens group, the optical path splitting element is disposed on an optical path of the lens group, the optical path splitting element includes an optical path splitting surface configured to form a first optical path and a second optical path, the first optical path is formed on a line extended from the optical path of the lens group, the second optical path is formed to cross the first optical path, an optical path length in the first optical path is different from an optical path length in the second optical path, a sum total of the number of transmissions of light and the number of reflections of light in the second optical path is larger than a sum total of the number of transmissions of light and the number of reflections of light in the first optical path, a first optical image formed in the first optical path and a second optical image formed in the second optical path are imaged with the image pickup element, the image processing device includes: an image correction processor configured to correct two images acquired by imaging such that differences of the two images other than focus are corrected to be substantially equal to each other; and an image composition processor configured to generate a composite image from the two images corrected by the image correction processor, and the image correction processor includes a tone correction unit configured to make relative luminance and saturation of the two images to substantially agree in at least one desired specific wavelength region.

The endoscope device according to the present invention is aimed at providing an endoscope device capable of acquiring an image with a small difference in brightness and a small difference in tone even when a difference in brightness and a difference in tone occur in a plurality of optical images.

Figure 11:
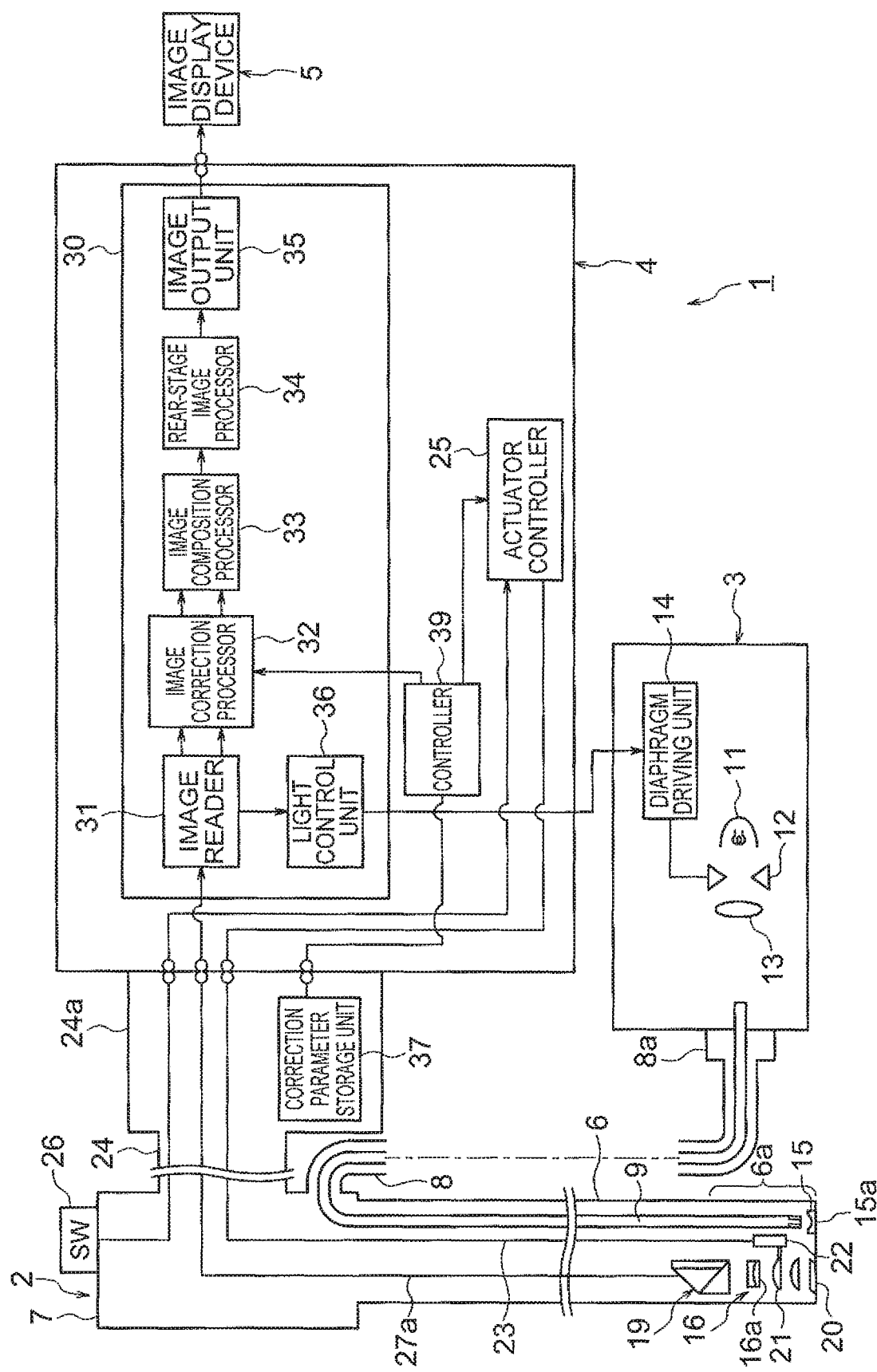
FIG. 11 is a diagram illustrating an endoscope device.

As illustrated in FIG. 11, an endoscope device 1 according to the present embodiment includes an endoscope 2 inserted into a subject, a light source device 3 configured to supply illumination light to the endoscope 2, a processor device 4, and an image display device 5.

The processor device 4 has a function of performing image processing, but also has other functions. The processor device 4 includes an actuator controller 25, an image processor 30, and a controller 39. The image display device 5 displays an image signal generated with the processor device 4 as an endoscope image.

The endoscope 2 includes an elongated insertion unit 6 to be inserted into the subject, and an operating unit 7 provided at the rear end of the insertion unit 6. A light guide cable 8 extends outward from the operating unit 7. One end of the light guide cable 8 is detachably connected with the light source device 3 through a connection unit 8a. The light guide cable 8 includes a light guide 9 therein. Part of the light guide 9 is disposed inside the insertion unit 6.

The light source device 3 includes therein a lamp 11, such as a xenon lamp, as the light source. The light source is not limited to the lamp 11, such as a xenon lamp, but a light emitting diode (abbreviated to "LED") may be used. The transmitted light quantity of the illumination light generated with the lamp 11, for example, white light, is regulated with a diaphragm 12. Thereafter, the illumination light is condensed with a condenser lens 13, and made incident on an incident end surface of the light guide 9. It is possible to change the aperture of the diaphragm 12 with a diaphragm driving unit 14.

The light guide 9 transmits the illumination light generated by the light source device 3 to a distal end portion 6a of the insertion unit 6. The transmitted illumination light is emitted from the distal end surface of the light guide 9. An illumination lens 15 is disposed in the distal end portion 6a while facing the distal end surface. The illumination lens 15 emits the illumination light from an illumination window 15a. In this manner, the observation target region inside the subject is illuminated.

An observation window 20 is provided adjacent to the illumination window 15a in the distal end portion 6a. Light from the observation target region passes through the observation window 20, and is made incident on the inside of the distal end portion 6a. The objective optical system is disposed behind the observation window 20. The objective optical system is formed of a lens group 16 and an optical path splitting unit 19.

The lens group 16 includes a lens 16a and a lens 21. The lens 21 is movable along the optical axis. In this manner, focusing is performed. An actuator 22 is disposed to move the lens 21.

One image pickup element (not illustrated) is disposed on the optical path splitting unit 19. Two optical images are simultaneously formed on the light-receiving surface of the image pickup element. The two optical images are imaged with the image pickup element.

The operating unit 7 is connected with the processor device 4 through a cable 24. A signal connector 24a is provided in a portion connected with the processor device 4.

Transmission of various types of information is performed between the endoscope 2 and the processor device 4 through the cable 24. The signal connector 24a includes a correction parameter storage unit 37.

The correction parameter storage unit 37 stores therein correction parameters (or information of correction parameters) used for correction of the image. The correction parameters are different between individual endoscopes. It is assumed that an endoscope having unique endoscope identification information is connected with the processor device 4. In this case, on the basis of the endoscope identification information, correction parameters peculiar to the connected endoscope are read from the correction parameter storage unit 37. Image correction is performed in an image correction processor 32 on the basis of the read correction parameters. Presence/absence of correction is determined by the controller 39.

Control of the actuator 22 is performed by the actuator controller 25. For this reason, the actuator 22 and the actuator controller 25 are connected through a signal line 23. Moreover, the image pickup element is connected with the image processor 30 through a signal line 27a. The signal from the image pickup element is input to the image processor 30. Information of a switch 26 provided in the operating unit 7 is also transmitted to the processor device 4 through a signal line.

When the optical path length in the first optical path is slightly different from the optical path length in the second optical path, two optical images in focus are formed in front of and behind the image pickup surface. The shift quantities of the optical images from the image pickup surface are slight. For this reason, two optical images in focus only in a part of the region are formed on the image pickup surface.

The two optical images are imaged with the image pickup element. An image signal acquired by imaging is input to the image processor 30 through the signal line 27a. The image processor 30 includes an image reader 31, the image correction processor 32, an image composition processor 33, a rear-stage image processor 34, an image output unit 35, and a light control unit 36.

In the image reader 31, image signals of a plurality of images are read from the input image signal. Herein, both the number of optical images and the number of images are two.

In the optical system forming two optical images, a geometrical difference may occur. Examples of the geometrical difference include a relative difference of the two optical images, such as a difference in magnification, a difference in position, and a difference in rotational direction. It is difficult to completely remove these differences in manufacturing of the objective optical system or the like. However, when the shift quantities of them increase, for example, a composite image looks double. For this reason, it is preferable to correct the geometrical difference described above in the image correction processor 32.

The image correction processor 32 performs image correction on the two read images. The image correction processor 32 performs, for example, processing to make at least one difference among a relative difference in magnification, a difference in position, and a difference in rotation agree between the two images.

In addition, the image correction processor 32 performs tone correction. For this reason, the image correction processor 32 includes atone correction unit (not illustrated). In tone correction, the tone correction unit performs processing to make relative luminance and saturation of the two images substantially agree in at least one desired specific wavelength band. The tone correction may be performed by the image correction processor 32, without providing the tone correction unit.

The image correction processor 32 changes the luminance in one of the two images to substantially agree with the luminance in the other image. Moreover, the image correction processor 32 changes the saturation in one of the images to substantially agree with the saturation in the other image.

As described above, in a method of acquiring an image with a large depth of field, only in-focus regions are extracted from a plurality of images, and composition of the extracted regions is performed. In the endoscope device according to the present embodiment, it is possible to reduce a difference in brightness and/or a difference in tone in a plurality of images. Accordingly, it is possible to reduce unevenness in brightness and/or a difference in tone in the composite image.

Moreover, in a method for improving the color reproducibility of the image, image composition using two images is performed. When a difference in brightness and/or a difference in tone occurs in two optical images, a difference in brightness and/or a difference in tone occurs also in two images acquired by imaging. In the endoscope device according to the present embodiment, it is possible to reduce a difference in brightness and a difference in tone, even when a difference in brightness and/or a difference in tone occurs in a plurality of images. Accordingly, it is possible to further improve color reproducibility of the composite image.

In the image composition processor 33, first, contrast is compared using two images. This comparison is performed on each of the spatially equal pixel regions in the two images. Thereafter, the pixel region with the relatively high contrast is selected. Thereafter, one image is generated using the selected pixel region. As just described, one composite image is generated from two images. When a difference in contrast between two images is small, it suffices to generate a composite image after performing composite image processing to provide each of the images with a predetermined weight and add the weight to the images.

The rear-stage image processor 34 performs image processing, such as edge enhancement and gamma correction, on the composite image. The image output unit 35 outputs the image-processed image to the image display device 5.

In the light control unit 36, a light control signal to control brightness of light to the standard brightness is generated from the image read with the image reader 31. The light control signal is output to the diaphragm driving unit 14 of the light source device 3. The diaphragm driving unit 14 regulates the opening quantity of the diaphragm 12 so as to maintain the standard brightness in accordance with the light control signal.

In the endoscope device according to the present embodiment, it is preferable that the luminance in the wavelength band of 640 nm or more and 760 nm or less be corrected.

In correction of luminance, a correction coefficient "KI=IB/IA" is calculated from luminance IA in an image A and luminance IB in an image B. Thereafter, the luminance in the image A is corrected using the correction coefficient KI.

Figure 12A:
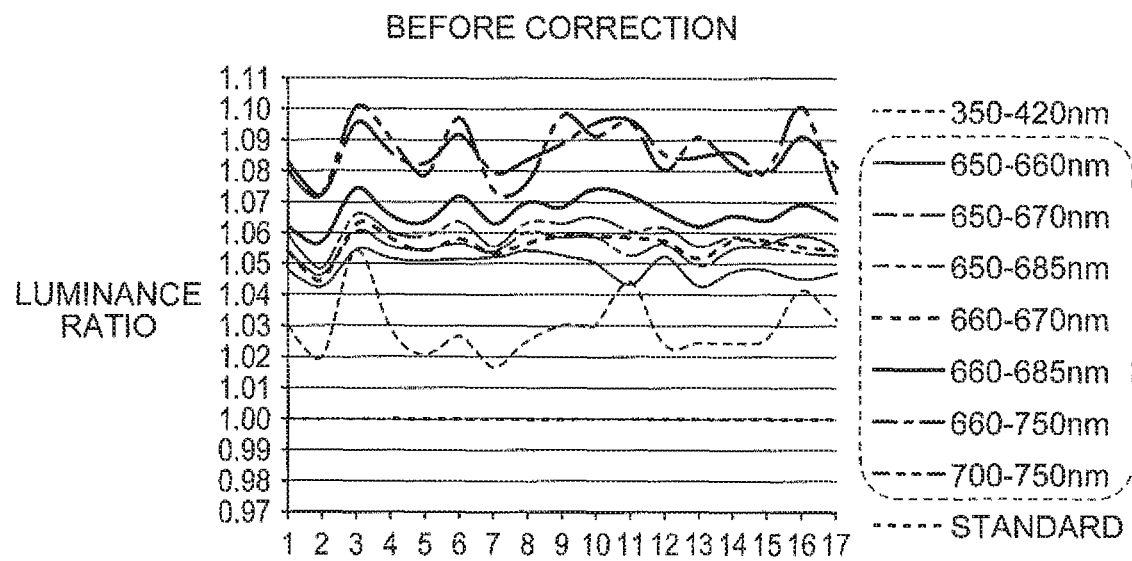
FIG. 12A and FIG. 12B are diagrams illustrating states of correction of luminance.
Figure 12B:
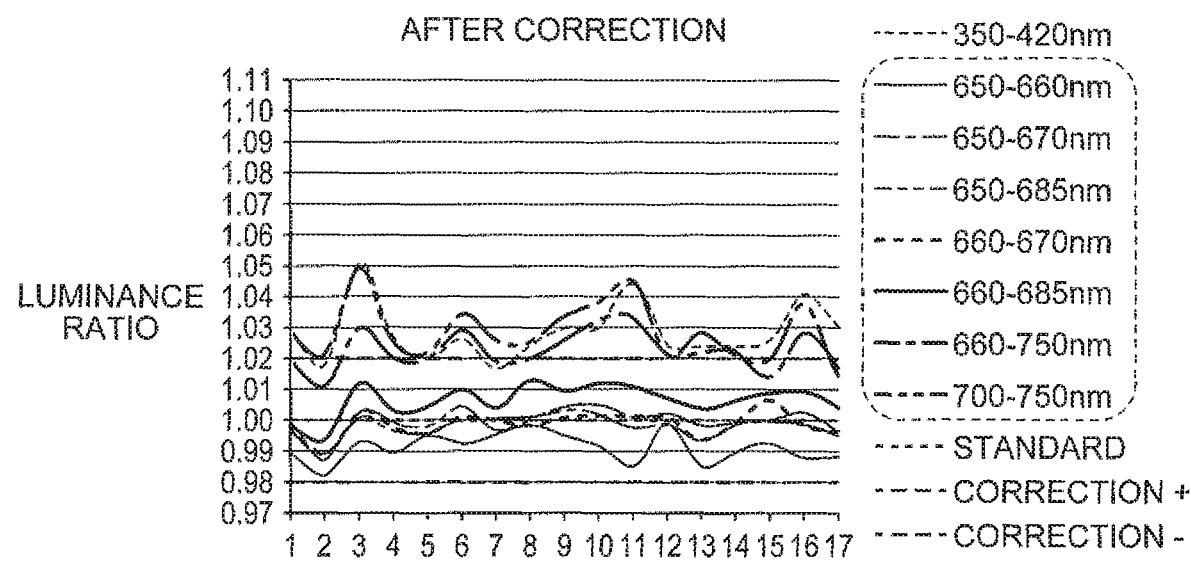

FIG. 12A and FIG. 12B illustrate states of correction of luminance. FIG. 12A is a diagram illustrating distribution of luminance ratios before correction, and FIG. 12B is a diagram illustrating distribution of luminance ratios after correction. In FIG. 12A and FIG. 12B, the vertical axis indicates the luminance ratio, and the horizontal axis indicates the position on the image.

It is possible to calculate a signal Y and a signal CrCb by using the signal output from the image pickup element. Because the signal Y indicates luminance, it is possible to acquire luminance from the signal Y. A plurality of pixels are required for calculation of the signal Y and the signal CrCb. For this reason, by setting a minute region formed of a plurality of pixels, the signal Y and the signal CrCb is calculated from the pixels included in the minute region. The position on the image means the position of the minute region.

In correction of luminance, the luminance in the image A is corrected such that the luminance ratio is brought close to 1. As illustrated in FIG. 12A and FIG. 12B, a wavelength band from 350 nm to 420 nm and a wavelength band from 650 nm to 750 nm are used in correction of luminance. As described later, the wavelength band from 650 nm to 750 nm is divided into seven wavelength bands. Accordingly, eight wavelength bands are used in correction of luminance.

When correction of luminance is performed in one broad wavelength band, accuracy of the correction value decreases. In this case, it is impossible to accurately perform correction of luminance. To acquire a correction value with high accuracy, it is necessary to enhance the wavelength resolution (to increase the number of samples) in the target wavelength range.

The wavelength band from 650 nm to 750 nm is a very broad wavelength band. For this reason, in the endoscope device according to the present embodiment, the broad wavelength band is divided into a plurality of wavelength bands to calculate a difference in luminance. In this manner, it is possible to derive a correction value with high accuracy in each of the wavelength bands. As a result, it is possible to accurately perform correction of luminance.

As illustrated with a frame of broken lines in FIG. 12A, in correction of luminance, the wavelength band from 650 nm to 750 nm is divided into seven wavelength bands to perform correction of luminance in each of the wavelength bands. A first wavelength band is a range from 650 nm to 660 nm. A second wavelength band is a range from 650 nm to 670 nm. A third wavelength band is a range from 650 nm to 685 nm. A fourth wavelength band is a range from 660 nm to 670 nm. A fifth wavelength band is a range from 660 nm to 685 nm. A sixth wavelength band is a range from 660 nm to 750 nm. A seventh wavelength band is a range from 700 nm to 750 nm.

As illustrated in FIG. 12B, with respect to the first wavelength band to the fifth wavelength band, the value of the luminance ratio in each of the wavelength bands has been brought close to 1.

As described above, in the endoscope, observation of the inside of the body is performed. The subject in the body looks reddish in many cases. Moreover, an image pickup element is used for imaging the subject. The sensitivity of the image pickup element increases as the wavelength becomes longer. Accordingly, the sensitivity thereof for red light is higher than the sensitivity for blue light and green light.

The first wavelength band to the fifth wavelength band substantially agree with the wavelength region of red light. Accordingly, with the value of the luminance ratio in each of the wavelength bands brought close to 1, it is possible to form a plurality of images with a small difference in brightness in the wavelength region of red light.

By using these images, it is possible to further improve the color reproducibility in the wavelength region of red light. Moreover, in an image with a large depth of field, it is possible to reduce unevenness of brightness in the wavelength region of red light.

In the seven wavelength bands, the wavelength regions overlap in at least two wavelength bands. For example, in the first wavelength band and the second wavelength band, the ranges from 650 nm to 660 nm overlap. When the second wavelength band is narrowed to remove the overlap, the luminance of the image in the second wavelength band decreases. When the luminance of the image becomes too low, it becomes difficult to discriminate luminance from noise. By providing the second wavelength band with the wavelength band overlapping the first wavelength band, it is possible to prevent decrease in luminance of the image.

In a case where a broad wavelength band is divided into a plurality of wavelength bands, when the number of divided bands is too large, luminance of the image in one wavelength band decreases. In this case, because the correction value includes a large error, it is impossible to acquire a correction value with high accuracy. Moreover, the processing circuit becomes complicated.

In the endoscope device according to the present embodiment, it is preferable to perform correction such that the luminance ratio after correction falls within a range of 0.98 or more and 1.02 or less.

In this manner, it is possible to further improve the color reproducibility in the wavelength region of red light. Moreover, in an image with a large depth of field, it is possible to further reduce unevenness in brightness in the wavelength region of red light.

As illustrated in FIG. 12B, in each of the wavelength bands from the first wavelength band to the fifth wavelength band, the luminance ratio after correction falls within a range of 0.98 or more and 1.02 or less. In this manner, it is possible to acquire an image with a small difference in brightness in ordinary observation.

It is preferable to bring the ratio to close to 1, also with respect to the luminance ratio in the sixth wavelength band and the luminance ratio in the seventh wavelength band. In this manner, it is possible to acquire an image with a smaller difference in brightness.

In the endoscope device according to the present embodiment, it is preferable to correct saturation in a wavelength band of 640 nm or more and 760 nm or less.

In change of saturation, a correction coefficient "KC=CB/CA" is calculated from the saturation CA in the image A and the saturation CB in the image B. Thereafter, saturation in the image A is corrected using the correction coefficient KC.

Figure 13A:
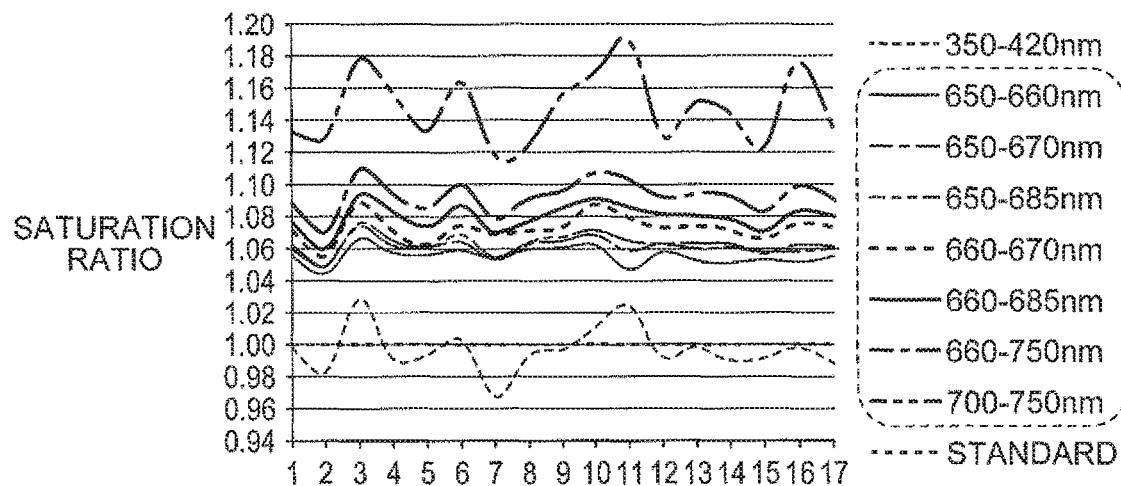
FIG. 13A and FIG. 13B are diagrams illustrating states of correction of saturation.
Figure 13B:
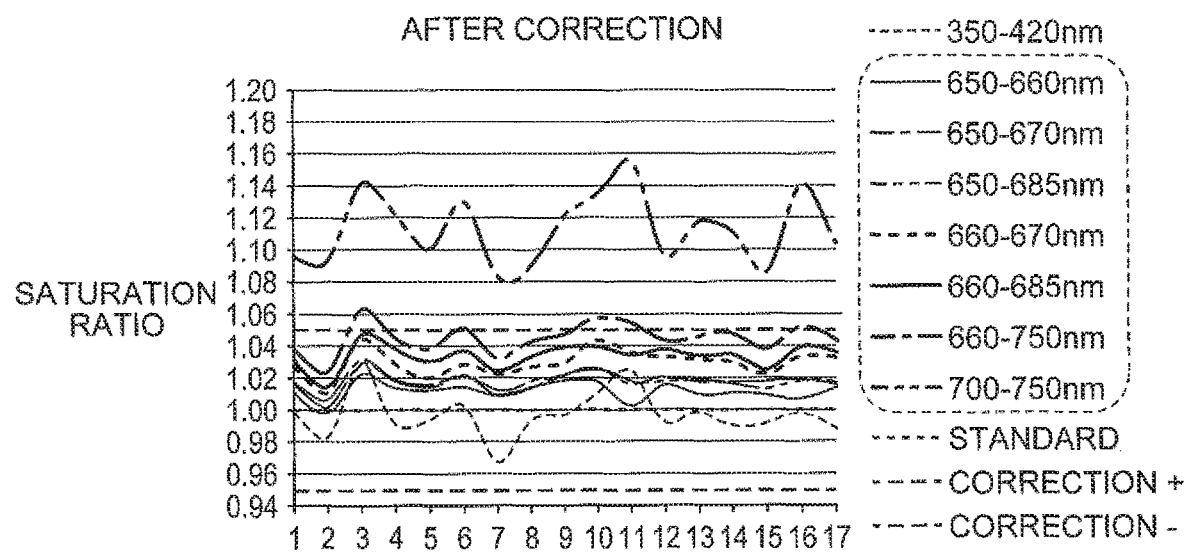

FIG. 13A and FIG. 13B illustrate state of correction of saturation. FIG. 13A is a diagram illustrating distribution of saturation ratios before correction, and FIG. 13B is a diagram illustrating distribution of saturation ratios after correction.

In FIG. 13A and FIG. 13B, the vertical axis indicates the saturation ratio, and the horizontal axis indicates the position on the image. The position on the image is as explained with FIG. 12A and FIG. 12B. As described above, it is possible to calculate the signal Y and the signal CrCb from the output signal from the image pickup element. Because the signal CrCb is a signal relating to color, it is possible to calculate saturation from the signal CrCb.

Eight wavelength bands are also used in correction of saturation. Moreover, in the same manner as correction of luminance, the range from 650 nm to 750 nm is divided into seven wavelength bands, and correction of saturation is performed in each of the wavelength bands. Also in correction of saturation, the saturation in the image A is corrected such that the saturation ratio is brought close to 1.

A first wavelength band is a range from 650 nm to 660 nm. A second wavelength band is a range from 650 nm to 670 nm. A third wavelength band is a range from 650 nm to 685 nm. A fourth wavelength band is a range from 660 nm to 670 nm. A fifth wavelength band is a range from 660 nm to 685 nm. A sixth wavelength band is a range from 660 nm to 750 nm. A seventh wavelength band is a range from 700 nm to 750 nm.

As illustrated in FIG. 13B, with respect to the first wavelength band to the sixth wavelength band, the value of the saturation ratio in each of the wavelength bands has been brought close to 1.

As described above, in the endoscope, observation of the inside of the body is performed. The subject in the body looks reddish in many cases. Moreover, an image pickup element is used for imaging the subject. The sensitivity of the image pickup element increases as the wavelength becomes longer. Accordingly, the sensitivity thereof for red light is higher than the sensitivity for blue light and green light.

The first wavelength band to the sixth wavelength band substantially agree with the wavelength region of red light. Accordingly, with the value of the saturation ratio in each of the wavelength bands brought close to 1, it is possible to form a plurality of images with a small difference in tone in the wavelength region of red light.

By using these images, it is possible to further improve the color reproducibility in the wavelength region of red light. Moreover, in an image with a large depth of field, it is possible to reduce a difference in tone in the wavelength region of red light.

Also in correction of saturation, the wavelength band ranging from 650 nm to 750 nm is divided into seven wavelength bands. Moreover, in the seven wavelength bands, the wavelength regions overlap in at least two wavelength bands. The reason for adopting such a configuration is as explained in correction of luminance. In this manner, it is possible to derive a correction value with high accuracy in each of the wavelength bands. As a result, it is possible to accurately perform correction of saturation.

In the endoscope device according to the present embodiment, it is preferable to perform correction such that the saturation ratio after correction falls within a range of 0.95 or more and 1.05 or less.

In this manner, it is possible to further improve the color reproducibility in the wavelength region of red light. Moreover, in an image with a large depth of field, it is possible to further reduce a difference in tone in the wavelength region of red light.

As illustrated in FIG. 13B, in each of the wavelength bands from the first wavelength band to the fifth wavelength band, the luminance ratio after correction falls within a range of 0.95 or more and 1.05 or less. In this manner, it is possible to acquire an image with a small difference in tone in ordinary observation.

It is preferable to bring the ratio to close to 1, also with respect to the luminance ratio in the sixth wavelength band and the saturation ratio in the seventh wavelength band. In this manner, it is possible to acquire an image with a smaller difference in tone.

In the endoscope device according to the present embodiment, it is preferable to correct luminance in a wavelength band ranging from 400 nm to 450 nm.

In this manner, it is possible to further improve the color reproducibility in narrow-band observation. Moreover, in an image with a large depth of field, it is possible to further reduce unevenness in brightness in narrow-band observation.

In the endoscope device according to the present embodiment, it is preferable to correct saturation in a wavelength band ranging from 400 nm to 450 nm.

In this manner, it is possible to further improve the color reproducibility in narrow-band observation. Moreover, in an image with a large depth of field, it is possible to further reduce a difference in tone in narrow-band observation.

In the endoscope device according to the present embodiment, it is preferable that the optical surface satisfying the following conditional expression (1) be positioned on the first optical path:

$$0.8 \leq MR650/MR550 \leq 0.9 \quad (1)$$

where,
MR550 is the reflectivity at a wavelength of 550 nm, and
MR650 is the reflectivity at a wavelength of 650 nm.

As described above, by locating the optical surface satisfying the conditional expression (1) on the first optical path, it is possible to set the first spectral characteristic substantially equal to the second spectral characteristic. As a result, it is possible to form a plurality of optical images having a small difference in brightness and/or a small difference in tone.

When a difference in brightness and/or a difference in tone is slightly left in the optical image, the difference in brightness and/or the difference in tone is slightly left also in the image acquired by imaging. For this reason, with the tone correction unit, the relative luminance and saturation of the images are made to substantially agree in at least one desired specific wavelength band.

In this manner, it is possible to further improve the color reproducibility. Moreover, in an image with a large depth of field, it is possible to further reduce unevenness in brightness and a difference in tone.

Various embodiments of the present invention have been described above, but the present invention is not limited to these embodiments. Embodiments formed of proper combinations of the structures of these embodiments within the range not departing from the gist of the invention also fall under the scope of the invention.

(Note)

The inventions of the following structures are derived from these examples.

(Appended Mode 1)

An objective optical system comprising:

a lens group configured to form an image of an object; and an optical path splitting element disposed on an image side of the lens group, wherein the optical path splitting element is disposed on an optical path of the lens group, the optical path splitting element includes an optical path splitting surface configured to form a first optical path and a second optical path, the first optical path is formed on a line extended from the optical path of the lens group, the second optical path is formed to cross the first optical path, an optical path length in the first optical path is different from an optical path length in the second optical path, a sum total of a number of transmissions of light and a number of reflections of light in the second optical path is larger than a sum total of a number of transmissions of light and a number of reflections of light in the first optical path, and an optical surface satisfying following conditional expression (1) is disposed on the first optical path, $$0.8 \leq MR650/MR550 \leq 0.9 \quad (1)$$

where,

MR550 is reflectivity at a wavelength of 550 nm, and

MR650 is reflectivity at a wavelength of 650 nm.

(Appended Mode 2)

The objective optical system according to appended mode 1, wherein an optical surface satisfying following conditional expression (2) is positioned on the first optical path:

$$0.75 \leq MRB \leq 0.80 \quad (2)$$

where,

MRB is reflectivity at a wavelength of 390 nm.

(Appended Mode 3)

The objective optical system according to appended mode 2, wherein the optical surface satisfying the conditional expression (1) and the optical surface satisfying the conditional expression (2) are an identical optical surface.

(Appended Mode 4)

The objective optical system according to any one of appended modes 1 to 3, wherein following conditional expression (3) is satisfied:

$$-0.15 \leq (B-A)/B \leq 0.15 \quad (3)$$

where,

B is transmissivity in a predetermined wavelength range of the first optical path, A is transmissivity in a predetermined wavelength range of the second optical path, and the predetermined wavelength range is a range from a wavelength of 400 nm to a wavelength of 700 nm.

(Appended Mode 5)

The objective optical system according to any one of appended modes 1 to 4, wherein a reflection surface and a ¼ wavelength plate are positioned on the second optical path, the ¼ wavelength plate is disposed between the optical path splitting surface and the reflection surface, and the optical surface has a characteristic of transmitting P-polarized light and reflecting S-polarized light.

(Appended Mode 6)

The objective optical system according to appended mode 5, wherein a depolarization element is disposed between the lens group and the optical path splitting element.

(Appended Mode 7)

The objective optical system according to any one of appended modes 1 to 5, wherein a dielectric multilayer film is formed on the optical surface satisfying the conditional expression (1).

(Appended Mode 8)

The objective optical system according to appended mode 6, wherein the optical surface satisfying the conditional expression (1) includes a metal reflective film, and the dielectric multilayer film is formed on the metal reflective film.

(Appended Mode 9)

The objective optical system according to any one of appended modes 1 to 8, further comprising:

an optical surface satisfying following conditional expression (4):

$$0.85 \leq MRUV \leq 0.9 \quad (4)$$

Where,

MRUV is reflectivity at a wavelength of 365 nm.

(Appended Mode 10)

The objective optical system according to any one of appended modes 1 to 9, wherein the optical surface satisfying the conditional expression (1) and the optical surface satisfying the conditional expression (4) are an identical optical surface.

(Appended Mode 11)

The objective optical system according to any one of appended modes 2 to 10, wherein the optical surface satisfying the conditional expression (2) and the optical surface satisfying the conditional expression (4) are an identical optical surface.

(Appended Mode 12)

An endoscope device comprising:

the objective optical system according to any one of appended modes 1 to 11;

an image pickup element; and an image processing device.

(Appended Mode 13)

An endoscope device comprising:

an objective optical system;

an image pickup element; and an image processing device, wherein the objective optical system includes:

a lens group configured to form an image of an object; and an optical path splitting element disposed on an image side of the lens group, the optical path splitting element is disposed on an optical path of the lens group, the optical path splitting element includes an optical path splitting surface configured to form a first optical path and a second optical path, the first optical path is formed on a line extended from the optical path of the lens group, the second optical path is formed to cross the first optical path, an optical path length in the first optical path is different from an optical path length in the second optical path, a sum total of a number of transmissions of light and a number of reflections of light in the second optical path is larger than a sum total of a number of transmissions of light and a number of reflections of light in the first optical path, a first optical image formed in the first optical path and a second optical image formed in the second optical path are imaged with the image pickup element, the image processing device includes:

an image correction processor configured to correct two images acquired by imaging such that differences of the two images other than focus are corrected to be substantially equal to each other; and an image composition processor configured to generate a composite image from the two images corrected by the image correction processor, and the image correction processor includes atone correction unit configured to make relative luminance and saturation of the two images to substantially agree in at least one desired specific wavelength region.

(Appended Mode 14)

The endoscope device according to appended mode 13, wherein luminance in a wavelength band ranging from 640 nm to 760 nm is corrected.

(Appended Mode 15)

The endoscope device according to appended mode 14, wherein correction is performed such that a luminance ratio after correction falls within a range of 0.98 or more and 1.02 or less.

(Appended Mode 16)

The endoscope device according to any one of appended modes 13 to 15, wherein saturation in a wavelength band ranging from 640 nm to 760 nm is corrected.

(Appended Mode 17)

The endoscope device according to appended mode 16, wherein correction is performed such that a saturation ratio after correction falls within a range of 0.95 or more and 1.05 or less.

(Appended Mode 18)

The endoscope device according to any one of appended modes 13 to 17, wherein luminance in a wavelength band ranging from 400 nm to 450 nm is corrected.

(Appended Mode 19)

The endoscope device according to any one of appended modes 13 to 18, wherein saturation in a wavelength band ranging from 400 nm to 450 nm is corrected.

(Appended Mode 20)

The endoscope device according to any one of appended modes 13 to 18, wherein an optical surface satisfying following conditional expression (1) is disposed on the first optical path, $$0.8 \leq MR650/MR550 \leq 0.9 \quad (1)$$

where,

MR550 is reflectivity at a wavelength of 550 nm, and
MR650 is reflectivity at a wavelength of 650 nm.

(Appended Mode 21)

An objective optical system comprising:

a lens group configured to form an image of an object; and
an optical path splitting element disposed on an image side of the lens group, wherein the optical path splitting element is disposed on an optical path of the lens group, the optical path splitting element includes an optical path splitting surface configured to form a first optical path and a second optical path, the first optical path is formed on a line extended from the optical path of the lens group, the second optical path is formed to cross the first optical path, an optical path length in the first optical path is different from an optical path length in the second optical path, a sum total of a number of transmissions of light and a number of reflections of light in the second optical path is larger than a sum total of a number of transmissions of light and a number of reflections of light in the first optical path, and an optical surface satisfying following conditional expression (2) is disposed on the first optical path, $$0.75 \leq MRB \leq 0.80 \quad (2)$$

Where,

MRB is reflectivity at a wavelength of 390 nm of the first optical path.

According to the present embodiment, it is possible to provide an objective optical system capable of forming a plurality of optical images with a small difference in brightness and a small difference in tone, and an endoscope device including the objective optical system.

The present invention is useful for an objective optical system capable of forming a plurality of optical images with a small difference in brightness and a small difference in tone, and an endoscope device including the objective optical system.

What is claimed is:

1. An objective optical system comprising:
a lens group configured to form an image of an object; and
an optical path splitting element disposed on an image side of the lens group,
wherein:
the optical path splitting element is disposed on an optical path of the lens group,
the optical path splitting element includes an optical path splitting surface configured to form a first optical path and a second optical path,
the first optical path is formed on a line extended from the optical path of the lens group,
the second optical path is formed to cross the first optical path,
an optical path length in the first optical path is different from an optical path length in the second optical path,
a sum total of a number of transmissions of light and a number of reflections of light in the second optical path is larger than a sum total of a number of transmissions of light and a number of reflections of light in the first optical path, and
an optical surface satisfying following conditional expression (1) is disposed on the first optical path, $$0.8 \leq MR650/MR550 \leq 0.9 \quad (1)$$

where,

MR550 is reflectivity at a wavelength of 550 nm, and
MR650 is reflectivity at a wavelength of 650 nm.

2. The objective optical system according to claim 1, wherein an optical surface satisfying following conditional expression (2) is disposed on the first optical path, $$0.75 \leq MRB \leq 0.80 \quad (2)$$

where,
MRB is reflectivity at a wavelength of 390 nm.

3. An endoscope device comprising:
the objective optical system according to claim 1;
an image pickup element; and
an image processing device.

4. The objective optical system according to claim 1, wherein following conditional expression (3) is satisfied:

$$-0.15 \leq (B-A)/B \leq 0.15 \quad (3)$$

where,
B is transmissivity in a predetermined wavelength range of the first optical path,
A is transmissivity in a predetermined wavelength range of the second optical path, and
the predetermined wavelength range is a range from a wavelength of 400 nm to a wavelength of 700 nm.

5. The objective optical system according to claim 1, wherein:
a reflection surface and a ¼ wavelength plate are positioned on the second optical path,
the ¼ wavelength plate is disposed between the optical path splitting surface and the reflection surface, and
the optical surface has a characteristic of transmitting P-polarized light and reflecting S-polarized light.

6. The objective optical system according to claim 1, wherein a depolarization element is disposed between the lens group and the optical path splitting element.

7. The objective optical system according to claim 1, wherein a dielectric multilayer film is formed on the optical surface satisfying the conditional expression (1).

8. The objective optical system according to claim 7, wherein:
the optical surface satisfying the conditional expression (1) includes a metal reflective film, and
the dielectric multilayer film is formed on the metal reflective film.

9. The objective optical system according to claim 1, further comprising:
an optical surface satisfying following conditional expression (4):

$$0.85 \leq MRUV \leq 0.9 \quad (4)$$

where,
MRUV is reflectivity at a wavelength of 365 nm.

10. The objective optical system according to claim 9, wherein the optical surface satisfying the conditional expression (1) and the optical surface satisfying the conditional expression (4) are an identical optical surface.

11. The objective optical system according to claim 9, wherein:
an optical surface satisfying following conditional expression (2) is disposed on the first optical path,
the optical surface satisfying the conditional expression (2) and the optical surface satisfying the conditional expression (4) are an identical optical surface, $$0.75 \leq MRB \leq 0.80 \quad (2)$$

where,
MRB is reflectivity at a wavelength of 390 nm.

12. An image pick-up apparatus comprising:
the objective optical system according to claim 1.

13. An endoscope comprising:
the objective optical system according to claim 1.

14. An endoscope device comprising:
an objective optical system,
an image pickup element, and
an image processing device,
wherein the objective optical system includes:
a lens group configured to form an image of an object; and
an optical path splitting element disposed on an image side of the lens group,
wherein:
the optical path splitting element is disposed on an optical path of the lens group,
the optical path splitting element includes an optical path splitting surface configured to form a first optical path and a second optical path,
the first optical path is formed on a line extended from the optical path of the lens group,
the second optical path is formed to cross the first optical path,
an optical path length in the first optical path is different from an optical path length in the second optical path,
a sum total of a number of transmissions of light and a number of reflections of light in the second optical path is larger than a sum total of a number of transmissions of light and a number of reflections of light in the first optical path,
a first optical image formed in the first optical path and a second optical image formed in the second optical path are imaged with the image pickup element,
the image processing device includes:
an image correction processor configured to correct two images acquired by imaging such that differences of the two images other than focus are corrected to be substantially equal to each other; and
an image composition processor configured to generate a composite image from the two images corrected by the image correction processor, and
the image correction processor includes a tone correction unit configured to make relative luminance and saturation of the two images to substantially agree in at least one desired specific wavelength region.

* * * * *